(12) United States Patent
Tanahashi

(10) Patent No.: US 12,174,365 B2
(45) Date of Patent: Dec. 24, 2024

(54) IMAGING APPARATUS FOR ENDOSCOPE AND IMAGING SYSTEM

(71) Applicant: Sony Olympus Medical Solutions Inc., Tokyo (JP)

(72) Inventor: Fuminori Tanahashi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 331 days.

(21) Appl. No.: 17/670,519

(22) Filed: Feb. 14, 2022

(65) Prior Publication Data

US 2022/0299749 A1   Sep. 22, 2022

(30) Foreign Application Priority Data

Mar. 19, 2021 (JP) ................. 2021-046257

(51) Int. Cl.
| | | |
|---|---|---|
| *A61B 1/00* | (2006.01) | |
| *A61B 1/06* | (2006.01) | |
| *A61B 18/14* | (2006.01) | |
| *G02B 23/24* | (2006.01) | |
| *G02B 23/26* | (2006.01) | |
| *H04N 23/51* | (2023.01) | |

(Continued)

(52) U.S. Cl.
CPC ...... *G02B 23/2484* (2013.01); *A61B 1/00147* (2013.01); *A61B 1/0661* (2013.01); *A61B 18/1482* (2013.01); *G02B 23/243* (2013.01); *G02B 23/26* (2013.01); *H04N 23/51* (2023.01); *A61B 2018/00601* (2013.01); *A61B 2018/00982* (2013.01); *H04N 23/555* (2023.01)

(58) Field of Classification Search
CPC .. G02B 23/2484; G02B 23/243; G02B 23/26; H04N 23/555; A61B 2018/00601; A61B 18/1482; A61B 1/00147; A61B 1/0661; A61B 1/00105; A61B 1/04042; A61B 1/0011

See application file for complete search history.

(56) References Cited

U.S. PATENT DOCUMENTS

| | | | | |
|---|---|---|---|---|
| 5,609,561 A | * | 3/1997 | Uehara | A61B 1/125 |
| | | | | 348/75 |
| 2008/0300456 A1 | * | 12/2008 | Irion | A61B 1/0607 |
| | | | | 600/109 |

(Continued)

FOREIGN PATENT DOCUMENTS

| | | |
|---|---|---|
| JP | 2000-227559 A | 8/2000 |
| JP | 2018075461 A | 5/2018 |
| JP | 2018153472 A | 10/2018 |

*Primary Examiner* — Timothy J Neal
(74) *Attorney, Agent, or Firm* — XSENSUS LLP

(57) ABSTRACT

An imaging apparatus for endoscope includes: a coupler; an exterior casing connected to the coupler and extending along a first axis crossing an optical axis of an endoscope, the exterior casing having outer dimensions in a direction along the first axis greater than outer dimensions in a direction along the optical axis of the endoscope; an optical system; and an imaging unit. The exterior casing includes a first exterior part, a second exterior part, and a connector part. The optical system and the imaging unit are housed, in the exterior casing, side by side on the optical axis of the endoscope such that light of an image of a subject guided by the optical system is captured by the imaging unit.

20 Claims, 14 Drawing Sheets

(51) Int. Cl.
    *A61B 18/00*     (2006.01)
    *H04N 23/50*     (2023.01)

(56) References Cited

U.S. PATENT DOCUMENTS

2014/0275781 A1*   9/2014  Deng .................. A61B 1/0011
                                                                       600/109
2018/0263471 A1*   9/2018  Ohno ................. A61B 1/00105

* cited by examiner

IMAGING APPARATUS FOR ENDOSCOPE AND IMAGING SYSTEM

CROSS-REFERENCE TO RELATED APPLICATION

This application claims priority from Japanese Application No. 2021-046257, filed on Mar. 19, 2021, the contents of which are incorporated by reference herein in its entirety.

BACKGROUND

The present disclosure relates to an imaging apparatus for endoscope and an imaging system.

In a medical field or an industrial field, an imaging system that observes the inside of a subject such as a person or a mechanical structure is known (see, for example, JP 2000-227559 A).

An imaging system described in JP 2000-227559 A includes an endoscope that captures and emits an image of a subject in a subject, and an imaging apparatus for endoscope that holds the endoscope and captures the image of the subject emitted from the endoscope.

Here, the imaging apparatus for endoscope includes a coupler, an exterior casing, an optical system, and an imaging unit.

The coupler is a portion that holds the endoscope, and has a bottomed cylindrical shape to which an eyepiece of the endoscope may be fitted.

The exterior casing connects to the coupler and extends along a first axis that crosses the optical axis of the endoscope. Further, the exterior casing has outer dimensions in a direction along the first axis greater than outer dimensions in a direction along the optical axis of the endoscope.

The optical system is housed in the exterior casing and guides light of an image of a subject emitted from the endoscope.

The imaging unit captures an image of the subject through the optical system.

SUMMARY

In the imaging apparatus for endoscope described in JP 2000-227559 A, as an optical system that guides light of the image of a subject toward an imaging unit, a refractive optical system such as a prism that guides light of the image of the subject traveling along an optical axis of an endoscope by bending the image of the subject in a direction along the first axis is adopted. Therefore, optical performance would be lost.

Furthermore, in the imaging apparatus for endoscope described in JP 2000-227559 A, when assembling the imaging apparatus for endoscope, an operator needs to insert an optical system and an imaging unit into an exterior casing along a first axis that is a longitudinal direction of the exterior casing. Therefore, assemblability is poor.

Therefore, there is a demand for a technique capable of improving assemblability without losing optical performance.

According to one aspect of the present disclosure, there is provided an imaging apparatus for endoscope including: a coupler configured to hold an endoscope for capturing an image of a subject, and emit the image of the subject; an exterior casing connected to the coupler and extending along a first axis crossing an optical axis of the endoscope, the exterior casing having outer dimensions in a direction along the first axis greater than outer dimensions in a direction along the optical axis of the endoscope; an optical system configured to guide light of the image of the subject; and an imaging unit configured to capture the image of the subject through the optical system, wherein the exterior casing includes a first exterior part including a first side wall and a second side wall crossing the optical axis of the endoscope, a first opening in the first side wall, a second opening in the second side wall which is further away from the coupler than the first side wall, and a third opening in a third side wall crossing the first axis, a second exterior part connected to the first exterior part to seal the second opening side of the first exterior part, and a connector part connected to the first exterior part to seal the third opening side of the first exterior part and is configured to connect to a cable for transmitting an image signal output from the imaging unit, and the optical system and the imaging unit are housed, in the exterior casing, side by side on the optical axis of the endoscope such that the light of the image of the subject guided by the optical system is captured by the imaging unit.

According to another aspect of the present disclosure, there is provided an imaging system including: an endoscope configured to capture an image of a subject, and emit the image of the subject; and an imaging apparatus for endoscope connected to the endoscope and configured to capture the image of the subject emitted from the endoscope, wherein the imaging apparatus for endoscope includes a coupler configured to hold the endoscope, an exterior casing connected to the coupler and extending along a first axis crossing an optical axis of the endoscope, the exterior casing having outer dimensions in a direction along the first axis greater than outer dimensions in a direction along the optical axis of the endoscope, an optical system configured to guide light of the image of the subject, and an imaging unit configured to capture the image of the subject through the optical system, and the exterior casing includes a first exterior part including a first side wall and a second side wall crossing the optical axis of the endoscope, a first opening in the first side wall, a second opening in the second side wall which is further away from the coupler than the first side wall, and a third opening in a third side wall crossing the first axis, a second exterior part connected to the first exterior part to seal the second opening side of the first exterior part, and a connector part connected to the first exterior part to seal the third opening side of the first exterior part and is configured to connect to a cable for transmitting an image signal output from the imaging unit, and the optical system and the imaging unit are housed, in the exterior casing, side by side on the optical axis of the endoscope so that the light of the image of the subject guided by the optical system is captured by the imaging unit.

DETAILED DESCRIPTION

Figure 1:
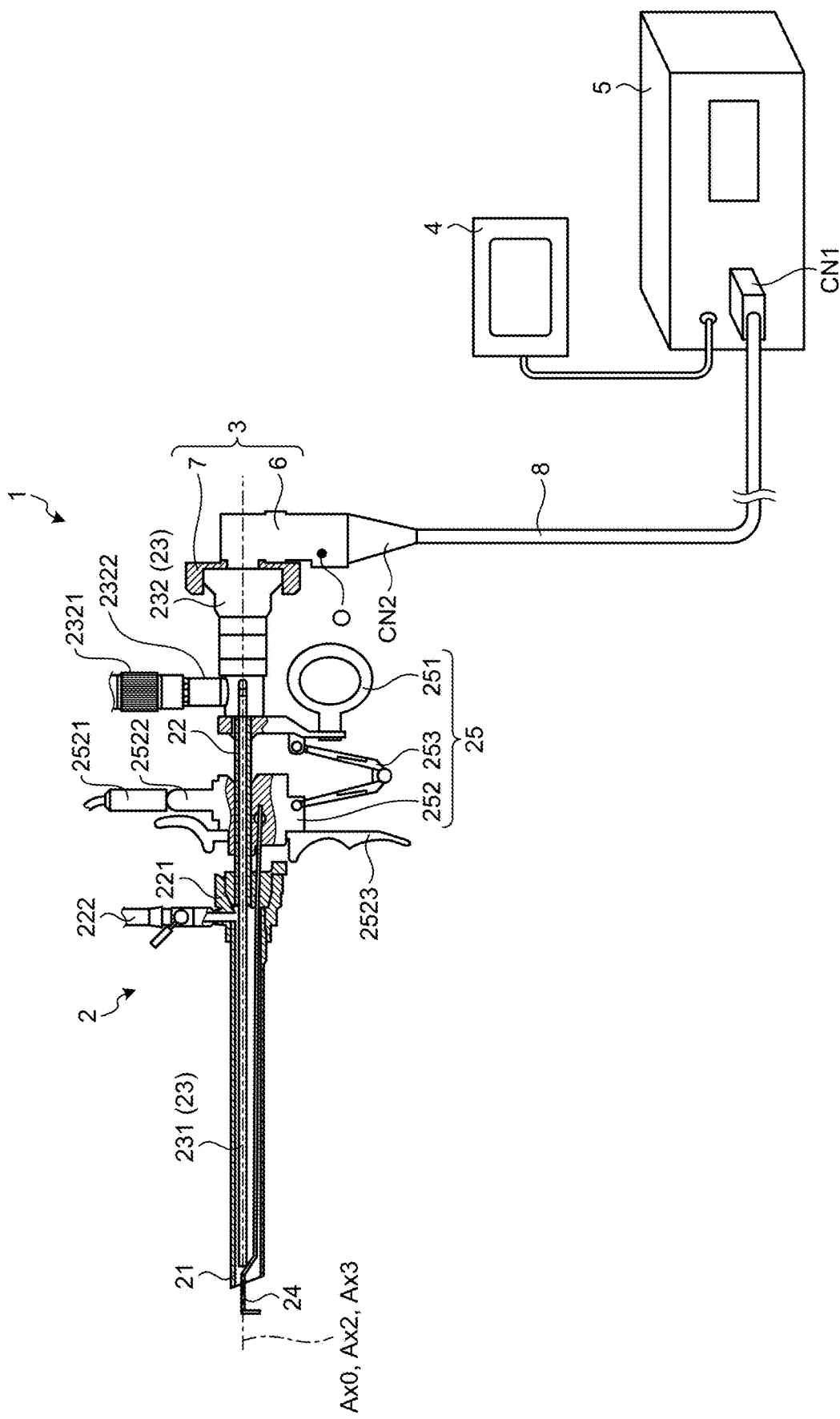
FIG. 1 is a view illustrating a configuration of an endoscope system according to a first embodiment.

Hereinafter, modes for carrying out the present disclosure (hereinafter, referred to as an embodiment) will be described with reference to the drawings. Note that the present disclosure is not limited by the embodiments described below. Furthermore, in the description of the drawings, the same portions are denoted by the same reference numerals.

First Embodiment

Schematic Configuration of Endoscope System

FIG. 1 is a view illustrating a configuration of an endoscope system according to a first embodiment.

An endoscope system 1 is used in the medical field, and is a device that treats (incises or the like) a living tissue while observing the inside of the living body. As illustrated in FIG. 1, the endoscope system 1 includes a resectoscope 2, an imaging apparatus 3 for endoscope, a display device 4, and a control device 5.

Note that the endoscope system 1 corresponds to an imaging system according to the present disclosure.

The resectoscope 2 is a portion that is inserted into a living body, captures an image of a subject, and treats a living tissue. As illustrated in FIG. 1, the resectoscope 2 includes a sheath 21, a guide tube 22, an endoscope 23, a resect electrode member 24, and a handle part 25.

The sheath 21 has a cylindrical shape and is a portion to be inserted into a living body.

The guide tube 22 has an outer diameter dimension smaller than the inner diameter dimension of the sheath 21, and is inserted into the sheath 21 from the proximal end side of the sheath 21 (right side in FIG. 1). Then, the distal end side of the guide tube 22 (left side in FIG. 1) is fixed to the proximal end side of the sheath 21 via a mounting member 221 (FIG. 1).

Here, the mounting member 221 is provided with a water supply port 222 for injecting liquid into the sheath 21 and supplying the liquid from a distal end of the sheath 21 (left end in FIG. 1).

The endoscope 23 is a portion that captures an image of a subject, and includes an insertion unit 231 and an eyepiece 232 as illustrated in FIG. 1.

The insertion unit 231 is fixed in the guide tube 22 and is inserted into the sheath 21. An optical system configured to use one or a plurality of lenses and condense light of an image of a subject is provided in the insertion unit 231.

The eyepiece 232 is connected to a proximal end of the insertion unit 231 (right end in FIG. 1). An eyepiece optical system (not illustrated) that emits an image of a subject collected by the optical system in the insertion unit 231 from the eyepiece 232 to the outside is provided in the eyepiece 232. The eyepiece 232 is formed in a tapered shape whose diameter is enlarged toward the side separated from the insertion unit 231 (right side in FIG. 1), and the imaging apparatus 3 for endoscope is detachably connected to the enlarged portion.

Here, as illustrated in FIG. 1, the eyepiece 232 is provided with a light source connector 2322 for connecting the light guide 2321. That is, the light supplied from the light source device (not illustrated) to the light guide 2321 is supplied to the insertion unit 231 via the eyepiece 232. The light supplied to the insertion unit 231 is emitted from the distal end of the insertion unit 231 (left end in FIG. 1) and emitted into the living body. The light emitted into the living body and reflected in the living body (the image of the subject) is taken into the insertion unit 231 from the distal end of the insertion unit 231 and emitted from the eyepiece 232 via the optical system (not illustrated) and the eyepiece optical system (not illustrated) in the insertion unit 231.

The resect electrode member 24 is inserted into the sheath 21 through the mounting member 221, and a distal end thereof (left end in FIG. 1) protrudes from the distal end of the sheath 21. Then, the distal end portion of the resect electrode member 24 comes into contact with the living tissue and treats the living tissue with a high-frequency current.

The handle part 25 is a portion where a doctor or the like grips the resectoscope 2 and operates the resect electrode member 24. As illustrated in FIG. 1, the handle part 25 includes a fixing ring 251, a slider 252, and a spring member 253.

The fixing ring 251 is a portion on which the doctor or the like hooks a thumb, and is fixed to the guide tube 22.

The slider 252 through which the guide tube 22 is inserted is configured to be movable in the left-right direction in FIG. 1 along the guide tube 22.

As illustrated in FIG. 1, the resect electrode member 24 is fixed to the slider 252. That is, the resect electrode member 24 moves toward and away in the left-right direction in FIG. 1 in the sheath 21 as the slider 252 moves.

In addition, a slider 252 is provided with a power supply connector 2522 for connecting a high frequency power supply cord 2521 that is connected to a high frequency power supply (not illustrated). The power supply connector 2522 is electrically connected to the resect electrode member 24 via a lead wire (not illustrated).

Further, as illustrated in FIG. 1, the slider 252 is provided with a finger hook member 2523 for the doctor or the like to hook a finger other than the thumb and move the slider 252 (move the resect electrode member 24 toward and away).

The spring member 253 has a substantially U shape, and has one end attached to the fixing ring 251 and the other end attached to the slider 252. The spring member 253 biases the slider 252 toward the side away from the fixing ring 251.

That is, the doctor or the like hooks the finger on the fixing ring 251 and the finger hook member 2523 and pulls the finger hook member 2523 against the biasing force of the spring member 253 to move the slider 252 to the right side in FIG. 1 (the resect electrode member 24 is moved to the right side in FIG. 1). On the other hand, when the doctor or the like releases the finger from the finger hook member 2523, the slider 252 (the resect electrode member 24) moves to the left side in FIG. 1 by the biasing force of the spring member 253.

The imaging apparatus 3 for endoscope is detachably connected to the eyepiece 232 of the resectoscope 2 (endoscope 23). Then, under the control of the control device 5, the imaging apparatus 3 for endoscope captures an image of a subject captured by the endoscope 23 (the image of the subject emitted from the eyepiece 232), and outputs an image signal obtained by the imaging (RAW signal).

Note that a detailed configuration of the imaging apparatus 3 for endoscope will be described in "Configuration of Imaging Apparatus for Endoscope" described later.

The display device 4 is configured using a display using liquid crystal, organic electro luminescence (EL), or the like. Then, the display device 4 displays an observation image or the like based on the video signal from the control device 5.

The control device 5 includes a central processing unit (CPU), a field-programmable gate array (FPGA), and the like, and integrally controls operations of the imaging apparatus 3 for endoscope, the display device 4, and a light source device (not illustrated). For example, the control device 5 performs predetermined image processing on the image signal (RAW signal) output from the imaging apparatus 3 for endoscope to generate a video signal for display. Then, the control device 5 causes the display device 4 to display the observation image based on the video signal. In addition, the control device 5 outputs a control signal, a synchronization signal, a clock, power, and the like to the imaging apparatus 3 for endoscope.

Configuration of Imaging Apparatus for Endoscope

Next, a detailed configuration of the imaging apparatus 3 for endoscope will be described.

Figure 2:
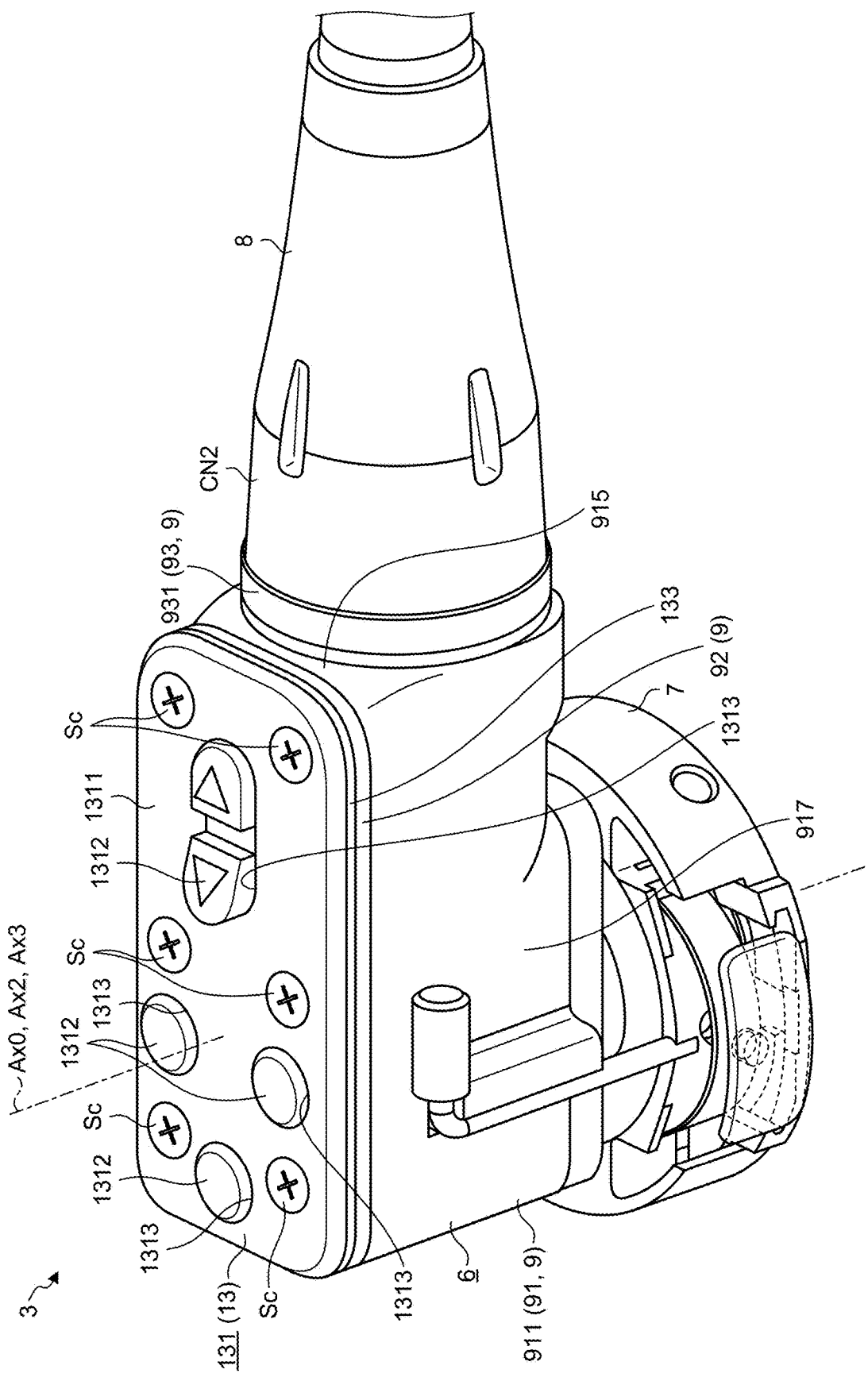
FIG. 2 is a view illustrating an imaging apparatus for endoscope.
Figure 3:
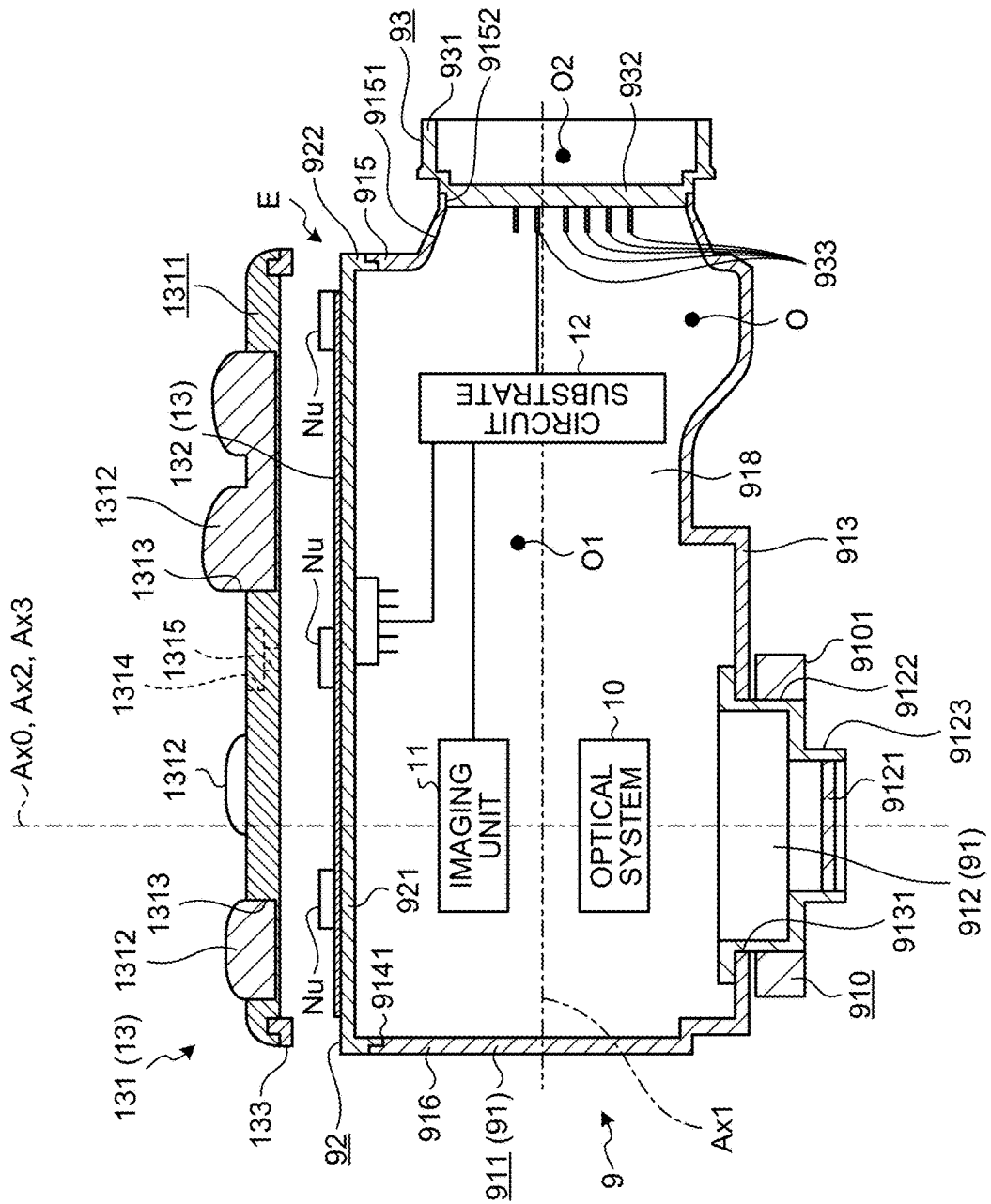
FIG. 3 is a view illustrating the imaging apparatus for endoscope.
Figure 4:
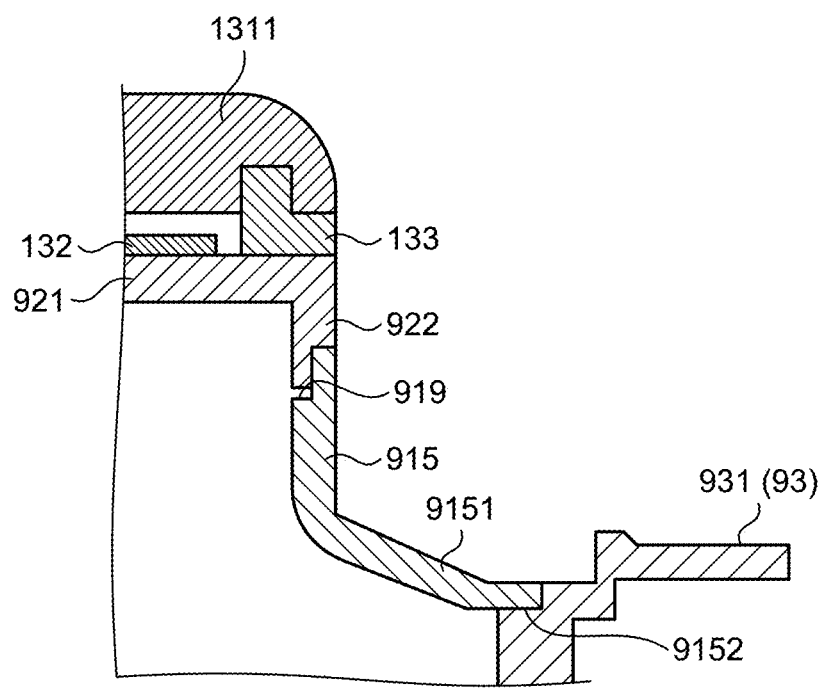
FIG. 4 is a view illustrating the imaging apparatus for endoscope.
Figure 5:
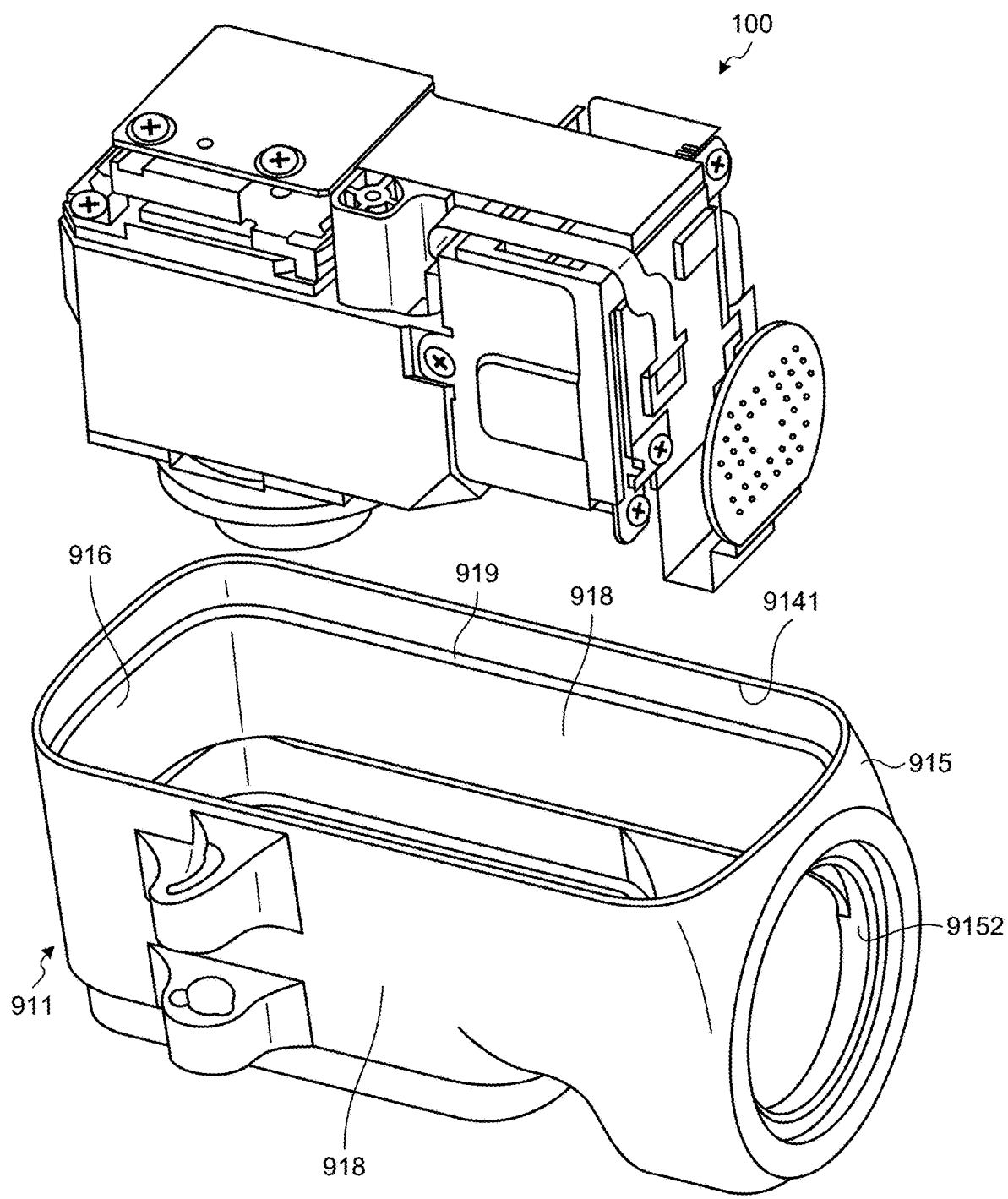
FIG. 5 is a view illustrating the imaging apparatus for endoscope.

FIGS. 2 to 5 are views illustrating an imaging apparatus 3 for endoscope. Specifically, FIG. 2 is a perspective view illustrating the appearance of the imaging apparatus 3 for endoscope. FIG. 3 is a cross-sectional view of an exterior casing 9 taken along a plane including an optical axis $Ax0$ of the endoscope 23. FIG. 4 is an enlarged view of a portion indicated by an arrow E in FIG. 3. FIG. 5 is a view illustrating a state in which an internal unit 100 is housed in a first exterior part 91.

As illustrated in FIGS. 1 to 5, the imaging apparatus 3 for endoscope includes an imaging apparatus main body 6, a coupler 7 (FIGS. 1 and 2), and a cable 8 (FIGS. 1 and 2).

The imaging apparatus main body 6 is a portion that is connected to the coupler 7 so as to be relatively rotatable about the optical axis $Ax0$ of the endoscope 23 (FIGS. 1 to 3 and 5) and captures an image of a subject emitted from the endoscope 23. As illustrated in FIGS. 2 to 5, the imaging apparatus main body 6 includes the exterior casing 9, an optical system 10 (FIG. 3), an imaging unit 11 (FIG. 3), a circuit substrate 12 (FIG. 3), an operating unit 13 (FIGS. 2 to 4), and a mounting bush 14 (see, for example, FIGS. 9, 10, and 13).

The exterior casing 9 is a casing that houses the optical system 10, the imaging unit 11, and the circuit substrate 12 therein. In addition, as illustrated in FIG. 2, the exterior casing 9 extends along a first axis $Ax1$ crossing the optical axis $Ax0$ of the endoscope 23, and has outer dimensions in a direction along the first axis $Ax1$ greater than outer dimensions in a direction along the optical axis $Ax0$ of the endoscope 23. As illustrated in FIGS. 2 to 5, the exterior casing 9 includes the first exterior part 91, a second exterior part 92 (FIGS. 2 to 4), and a connector part 93 (FIGS. 2 to 4).

As illustrated in FIGS. 2 to 5, the first exterior part 91 includes an exterior part main body 911 and a front exterior part 912 (FIG. 3).

The exterior part main body 911 is a container-shaped member made of a metal such as aluminum, an aluminum alloy, stainless steel, titanium, or a titanium alloy. More specifically, the exterior part main body 911 has a substantially rectangular parallelepiped shape extending along the first axis $Ax1$.

In the exterior part main body 911, as illustrated in FIG. 3, a first opening 9131 penetrating the inside and outside of the exterior part main body 911 is provided in a first side wall 913 on a side crossing the optical axis $Ax0$ of the endoscope 23 and approaching the coupler 7 (lower side in FIG. 3).

In addition, in the exterior part main body 911, the second side wall crossing the optical axis $Ax0$ of the endoscope 23 and facing the first side wall 913 is entirely deleted as illustrated in FIG. 3. That is, a second opening 9141 penetrating the inside and the outside of the exterior part main body 911 is provided in the portion where the second side wall existed. That is, the second side wall includes a virtual wall (virtual plane) formed by the second opening 9141 in a space facing the first side wall 913. The first and second openings 9131 and 9141 are provided on the surfaces of the first side wall 913 and the second side wall facing each other.

Further, in the exterior part main body 911, at an end of a rectangular frame shape on the second exterior part 92 side (upper side in FIG. 3) configured by the first side wall 913 and the four side walls 915 to 918 other than the second side wall, a recess 919 (FIG. 4) in which an inner portion of the rectangular frame is recessed downward in FIG. 3 is provided. That is, the end of the rectangular frame shape is formed in a stepped shape.

Among the four side walls 915 to 918, the third side wall 915 crossing the first axis $Ax1$ is provided with a bulging part 9151 bulging toward the outside of the exterior part main body 911 as illustrated in FIG. 3. Further, a third opening 9152 penetrating the inside and the outside of the exterior part main body 911 is provided on a projecting end portion of the bulging part 9151.

Here, the second opening 9141 has an opening area larger than that of the third opening 9152. Then, as described later, when assembling the imaging apparatus 3 for endoscope, the operator may insert the internal unit 100 into the exterior part main body 911 along the optical axis $Ax0$ of the endoscope 23 from the second opening 9141.

The front exterior part 912 has a substantially cylindrical shape made of a metal such as aluminum, an aluminum alloy, stainless steel, titanium, or a titanium alloy. Then, the front exterior part 912 is fixed to the exterior part main body 911 by welding between the outer surface of the front exterior part 912 and the first side wall 913 in a state of protruding to the outside of the exterior part main body 911 (coupler 7 side) through the first opening 9131. In this state, a central axis $Ax2$ of the front exterior part 912 coincides with the optical axis $Ax0$ of the endoscope 23.

As illustrated in FIG. 3, an optical element 9121 such as sapphire glass is fixed in the front exterior part 912. That is, the front exterior part 912 and the optical element 9121 hermetically seal the first opening 9131 side of the exterior part main body 911.

In addition, as illustrated in FIG. 3, the outer surface of the front exterior part 912 is formed in a stepped shape in which the proximal end side (upper side in FIG. 3) is larger in outer diameter dimension than the distal end side (lower side in FIG. 3). Hereinafter, for convenience of description, in the outer surface of the front exterior part 912, a cylindrical surface having a large outer diameter dimension on the proximal end side is referred to as a large diameter surface 9122 (FIG. 3), and a cylindrical surface having a small outer diameter dimension on the distal end side is referred to as a small diameter surface 9123 (FIG. 3).

Although not specifically illustrated, the small diameter surface 9123 is provided with a screw groove.

As illustrated in FIG. 3, a sliding member 910 is fixed to the front exterior part 912.

The sliding member 910 is made of a resin material and has an annular shape. The sliding member 910 surrounds the large diameter surface 9122 and is fixed at a position facing the large diameter surface 9122. In addition, in the sliding member 910, the surface facing the coupler 7 is constituted by a flat surface facing the optical axis Ax0 of the endoscope 23. Hereinafter, for convenience of description, the surface is referred to as a casing-side slide surface 9101 (FIG. 3).

The second exterior part 92 includes a metal such as aluminum, an aluminum alloy, stainless steel, titanium, or a titanium alloy. As illustrated in FIG. 3, the second exterior part 92 includes a base part 921 and a protruding part 922.

The base part 921 is formed of a plate body having a rectangular shape in plan view which is the same as an end having a rectangular frame shape on the second exterior part 92 side which is formed of the four side walls 915 to 918 of the exterior part main body 911.

The protruding part 922 is a portion protruding from an outer edge portion of one plate surface of the base part 921 in the normal direction of the plate surface. That is, the protruding part 922 has a rectangular frame shape same as an end having a rectangular frame shape on the second exterior part 92 side which is formed of the four side walls 915 to 918 of the exterior part main body 911. Further, the projecting end portion in the protruding part 922 is formed in a stepped shape corresponding to the end of the rectangular frame shape, and may be fitted to the end of the rectangular frame shape. Then, the second exterior part 92 is fixed to the exterior part main body 911 by welding between the protruding part 922 and the end of the rectangular frame shape in a state where the protruding part 922 is fitted to the end of the rectangular frame shape. That is, the second exterior part 92 hermetically seals the second opening 9141 side of the exterior part main body 911.

Further, in the second exterior part 92, as illustrated in FIG. 3, a plurality of nuts Nu is fixed to the other plate surface exposed to the outside by welding.

In the first embodiment, the connector part 93 is configured by a hermetic connector. Specifically, the connector part 93 includes a cylindrical outer frame 931, a plate body 932 that closes the outer frame 931, and a plurality of conductive pins 933 that penetrates front and back surfaces of the plate body 932, is attached to the plate body 932 in a state of being insulated from each other, and is electrically connected to the circuit substrate 12. Here, the outer frame 931 includes a metal such as aluminum, an aluminum alloy, stainless steel, titanium, or a titanium alloy. Then, the outer frame 931 is welded to the inner surface of the third opening 9152, whereby the connector part 93 is fixed to the exterior part main body 911. That is, the connector part 93 hermetically seals the third opening 9152 side of the exterior part main body 911.

Here, one end of the cable 8 is detachably connected to the control device 5 via a connector CN1 (FIG. 1), and the other end is detachably connected to the connector part 93 via a connector CN2 (FIGS. 1 and 2). The cable 8 transmits a signal, power, and the like between the imaging apparatus main body 6 and the control device 5.

The optical system 10 guides light of an image of a subject emitted from the endoscope 23. More specifically, the optical system 10 forms the image of the subject on an imaging surface of the imaging unit 11.

The imaging unit 11 includes an image sensor such as a charge coupled device (CCD) or a complementary metal oxide semiconductor (CMOS) that receives an image of a subject formed by the optical system 10 and converts the image of the subject into an electric signal under the control of the control device 5. Then, the imaging unit 11 outputs an image signal obtained by imaging under the control of the control device 5.

The optical system 10 and the imaging unit 11 described above are housed, as illustrated in FIG. 3, in the exterior casing 9, side by side on the optical axis Ax0 of the endoscope 23.

The circuit substrate 12 is electrically connected to the imaging unit 11, an operation board 132 constituting the operating unit 13, and the connector part 93 (the plurality of conductive pins 933). Then, the circuit substrate 12 drives the imaging unit 11 on the basis of a control signal output from the control device 5 and input via the cable 8 and the connector part 93 and an operation signal output from the operation board 132. In addition, the circuit substrate 12 processes the image signal output from the imaging unit 11 and transmits the processed image signal to the control device 5 via the connector part 93 and the cable 8.

As illustrated in FIG. 3, the circuit substrate 12 described above is housed at a position away from the optical axis Ax0 of the endoscope 23 and close to the connector part 93 in the exterior casing 9. Further, a center position O2 (FIG. 3) of the connector part 93 is located at a position closer to the coupler 7 (endoscope 23) than a center position O1 (FIG. 3) in a direction along the optical axis Ax0 of the endoscope 23 in the exterior casing 9. As a result, the center of gravity O (FIGS. 1 and 3) of the imaging apparatus 3 for endoscope is located at a position shifted from the optical axis Ax0 of the endoscope 23 and is located closer to the coupler 7 than the center position O1.

As illustrated in FIG. 5, the optical system 10, the imaging unit 11, and the circuit substrate 12 described above are integrated into the internal unit 100. Then, when assembling the imaging apparatus 3 for endoscope, the operator inserts the internal unit 100 into the exterior part main body 911 along the optical axis Ax0 of the endoscope 23 from the second opening 9141. Thereafter, the operator fixes the front exterior part 912, the second exterior part 92, and the connector part 93 to the exterior part main body 911 by welding at the above-described positions. As a result, the imaging apparatus 3 for endoscope is assembled.

The operating unit 13 is a portion that receives an operation by a user such as a doctor. As illustrated in FIGS. 2 to 4, the operating unit 13 includes a button unit 131 and the operation board 132.

As illustrated in FIGS. 2 to 4, the button unit 131 includes a button frame 1311 and a plurality of buttons 1312 (FIGS. 2 and 3).

The button frame 1311 is formed of a rectangular plate body having a planar size substantially the same as the planar size of the base part 921, and is arranged in a state of being stacked on the second exterior part 92 along the optical axis Ax0 of the endoscope 23. As illustrated in FIG. 2 or 3, the button frame 1311 is provided with a plurality of openings 1313 penetrating the front and back of the button frame 1311. In addition, the button frame 1311 is provided with a plurality of recesses 1314 (FIG. 3) recessed toward the second exterior part 92 side. Further, an insertion hole 1315 (FIG. 3) through which a screw Sc is inserted is provided in a bottom portion of the recess 1314.

The plurality of buttons 1312 is arranged in a state of being exposed to the outside through the plurality of openings 1313, and is portions that receive an operation by a user such as a doctor (are pressed by the user).

Then, the button unit 131 is attached to the exterior casing 9 as described below.

The operator fastens the screw Sc to the nut Nu through the insertion hole 1315 while interposing an annular (rectangular frame-shaped) packing 133 (FIGS. 2 to 4) between the button frame 1311 and the outer surface of the second exterior part 92. Thus, the button unit 131 is attached to the exterior casing 9. The packing 133 corresponds to a sealing member according to the present disclosure.

As illustrated in FIG. 3, the operation board 132 is attached to the outer surface of the second exterior part 92 and covered with the button frame 1311 and the packing 133. Although not specifically illustrated, a plurality of switch elements is mounted on the operation board 132 so as to correspond to the plurality of buttons 1312, respectively. Then, the operation board 132 outputs an operation signal corresponding to the operation of the button 1312 by the user such as a doctor to the circuit substrate 12.

Here, as illustrated in FIG. 3, the operation board 132 and the circuit substrate 12 are electrically connected to each other via a hermetic connector 134.

Figure 13:
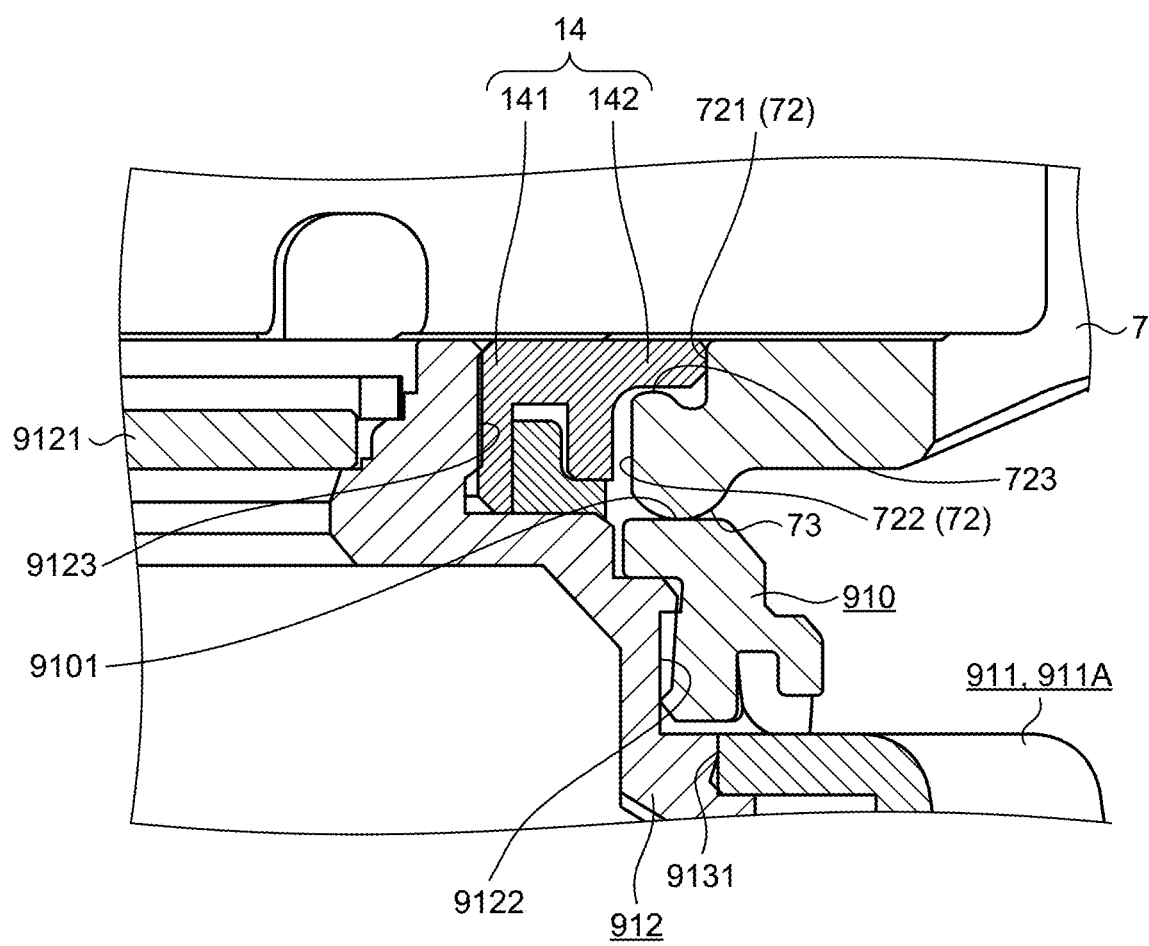
FIG. 13 is a view illustrating the first modification of the first and second embodiments.

The mounting bush 14 includes a bush main body 141 and a flange 142 (see, for example, FIG. 13).

The bush main body 141 is formed in a cylindrical shape having an inner diameter dimension substantially the same as the outer diameter dimension of the small diameter surface 9123. Further, a screw groove is provided on the inner peripheral surface of the bush main body 141.

The flange 142 has an annular shape projecting from an end on the coupler 7 side on the outer peripheral surface of the bush main body 141.

Then, the front exterior part 912 and the mounting bush 14 are fixed to each other by fastening a screw groove provided in the small diameter surface 9123 and a screw groove provided in the inner peripheral surface of the bush main body 141.

The coupler 7 is a portion that holds the endoscope 23, and has a bottomed cylindrical shape in which the eyepiece 232 may be fitted.

The pressing part 71 (see, for example, FIG. 9.) is provided on the inner peripheral surface of the coupler 7.

The pressing part 71 is movable in a direction of approaching and separating from a central axis Ax3 (FIGS. 2 and 3) of the coupler 7, and abuts on the outer peripheral surface of the eyepiece 232 fitted in the coupler 7 to press the eyepiece 232 toward the bottom portion of the coupler 7.

Then, in a state where the eyepiece 232 is fitted into the coupler 7, the optical axis Ax0 of the endoscope 23 coincides with the central axis Ax3 of the coupler 7.

In addition, a stepped through hole 72 (see, for example, FIG. 13) having an inner surface shape substantially the same as the outer surface shape of the mounting bush 14 is provided in the bottom portion of the coupler 7.

Hereinafter, for convenience of description, a peripheral edge portion of the through hole 72 on the outer surface of the coupler 7 will be referred to as a coupler-side slide surface 73 (see, for example, FIG. 13). The coupler-side slide surface 73 has an annular shape centered on the central axis Ax3 of the coupler 7.

The coupler 7 is attached to the imaging apparatus main body 6 as described below.

That is, with regard to the coupler 7, the operator inserts the front exterior part 912 into the through hole 72 in a posture in which the opening having the bottomed cylindrical shape is separated from the imaging apparatus main body 6. Then, the operator fixes the mounting bush 14 to the front exterior part 912 as described above. Thus, the coupler 7 is attached to the imaging apparatus main body 6. In this state, the central axis Ax3 of the coupler 7 substantially coincides with the central axis Ax2 of the front exterior part 912. Further, a specific clearance is provided between the casing-side slide surface 9101 and the coupler-side slide surface 73. Then, the coupler 7 is rotatable about the optical axis Ax0 of the endoscope 23 with respect to the imaging apparatus main body 6.

Therefore, the imaging apparatus main body 6 is rotatable about the optical axis Ax0 of the endoscope 23 with respect to the eyepiece 232 of the endoscope 23 via the coupler 7. In addition, since the center of gravity O of the imaging apparatus main body 6 is located at the above-described position, the imaging apparatus main body 6 is configured to rotate about the optical axis Ax0 regardless of the rotation of the endoscope 23 around the optical axis Ax0 in the resectoscope 2, and take a posture in which the center of gravity O is located below (on the vertical direction side) the optical axis Ax0.

According to the first embodiment described above, the following effects are obtained.

In the imaging apparatus 3 for endoscope according to the first embodiment, the optical system 10 and the imaging unit 11 are housed in the exterior casing 9, side by side on the optical axis Ax0 of the endoscope 23. That is, the optical system 10 is an optical system that guides light of an image of a subject traveling along the optical axis Ax0 of the endoscope 23 along the optical axis Ax0 and forms an image on the imaging surface of the imaging unit 11, and is not an optical system that employs a refractive optical system such as a prism as in the related art. Therefore, optical performance would not be lost.

Furthermore, in the imaging apparatus 3 for endoscope according to the first embodiment, in the first exterior part 91, the second opening 9141 is provided in the second side wall of the first side wall 913 and the second side wall, which cross the optical axis Ax0 of the endoscope 23 and face each other. Therefore, when assembling the imaging apparatus 3 for endoscope, the operator may insert the internal unit 100 into the exterior part main body 911 along the optical axis Ax0 of the endoscope 23 that is a transverse direction of the exterior part main body 911 from the second opening 9141. Therefore, assemblability may be improved.

As described above, according to the imaging apparatus 3 for endoscope according to the first embodiment, assemblability may be improved without losing optical performance.

In addition, in the imaging apparatus 3 for endoscope according to the first embodiment, the circuit substrate 12 is housed at a position away from the optical axis Ax0 of the endoscope 23 in the exterior casing 9. Further, the center position O2 of the connector part 93 is located at a position closer to the endoscope 23 than the center position O1 in a direction along the optical axis Ax0 of the endoscope 23 in the exterior casing 9. As a result, the center of gravity O of the imaging apparatus 3 for endoscope is located at a position shifted from the optical axis Ax0 of the endoscope 23 and is located closer to the endoscope 23 than the center position O1.

Therefore, it is possible to smoothly perform relative rotation of the imaging apparatus main body 6 and the coupler 7 about the optical axis Ax0 of the endoscope 23.

Meanwhile, in a case where the operating unit 13 is provided in the cable 8, there is the following first problem.

That is, at the time of using the endoscope system 1, a user such as a doctor, while operating the resectoscope 2, focuses on a target site to be treated with the resectoscope 2. For this reason, in a case where the user such as a doctor desires to operate the operating unit 13, it is difficult to look away from the target site. Therefore, it is necessary to search the operating unit 13 provided in the cable 8 using only own hands, and it takes time and effort to search the operating unit 13.

In addition, when the button unit 131 constituting the operating unit 13 is provided on an outer surface other than the outer surface of the second exterior part 92 in the exterior casing 9, there is the following second problem.

That is, when the endoscope system 1 is used, a user such as a doctor grips the handle part 25 of the resectoscope 2. In this state, when the button 1312 of the button unit 131 provided on the outer surface other than the outer surface of the second exterior part 92 in the exterior casing 9 is pressed, a force is applied to the button unit 131, so that the position of the distal end of the resectoscope 2 is shifted with the handle part 25 as a fulcrum, and the treatment may not be performed smoothly.

On the other hand, in the imaging apparatus 3 for endoscope according to the first embodiment, the button unit 131 is fixed to the outer surface of the second exterior part 92 via the packing 133 in a state of being stacked on the second exterior part 92 along the optical axis Ax0 of the endoscope 23.

Therefore, the first and second problems described above do not occur.

Second Embodiment

Next, a second embodiment will be described.

Hereinafter, the same reference numerals are given to the same configurations as those of the above-described first embodiment, and the detailed description thereof will be omitted or simplified.

In the second embodiment, the configurations of the exterior casing 9 and the operating unit 13 are changed from those of the imaging apparatus 3 for endoscope described in the first embodiment described above. Hereinafter, for convenience of description, the imaging apparatus 3 for endoscope according to the second embodiment will be referred to as an imaging apparatus 3A for endoscope. The exterior casing 9 according to the second embodiment is referred to as an exterior casing 9A. Further, the operating unit 13 according to the second embodiment will be referred to as an operating unit 13A.

Figure 6:
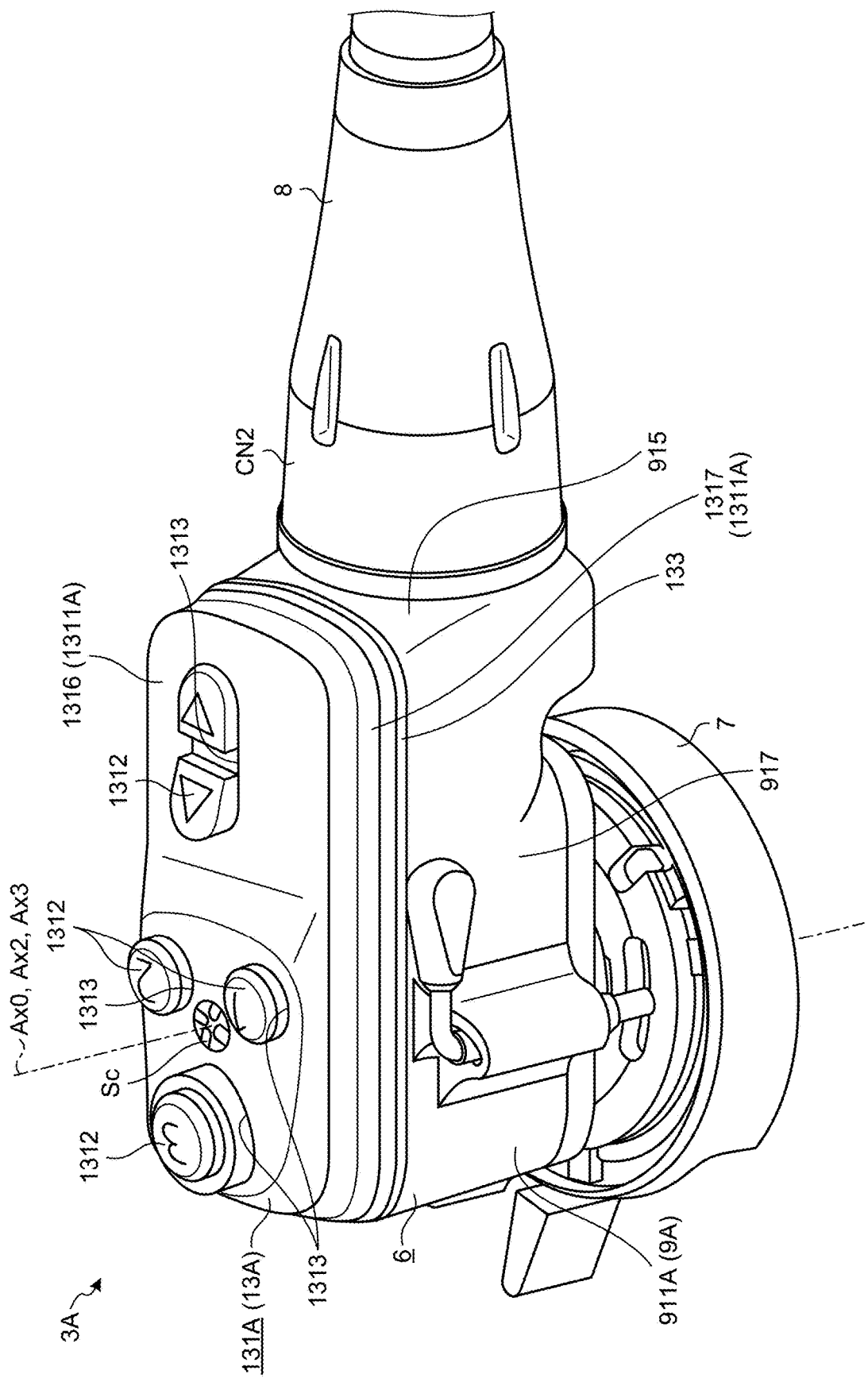
FIG. 6 is a view illustrating an imaging apparatus for endoscope according to a second embodiment.
Figure 7:
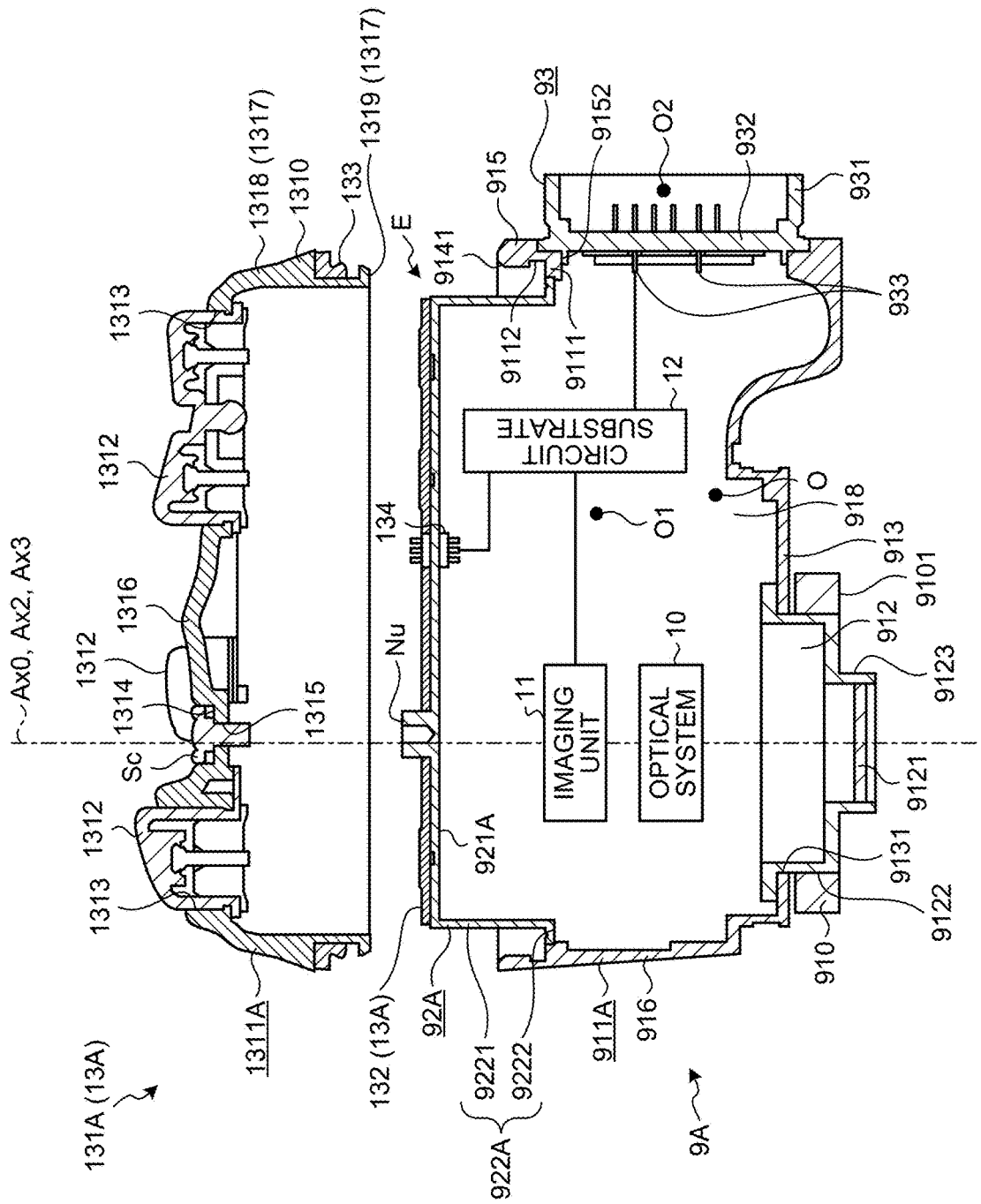
FIG. 7 is a view illustrating the imaging apparatus for endoscope according to the second embodiment.
Figure 8:
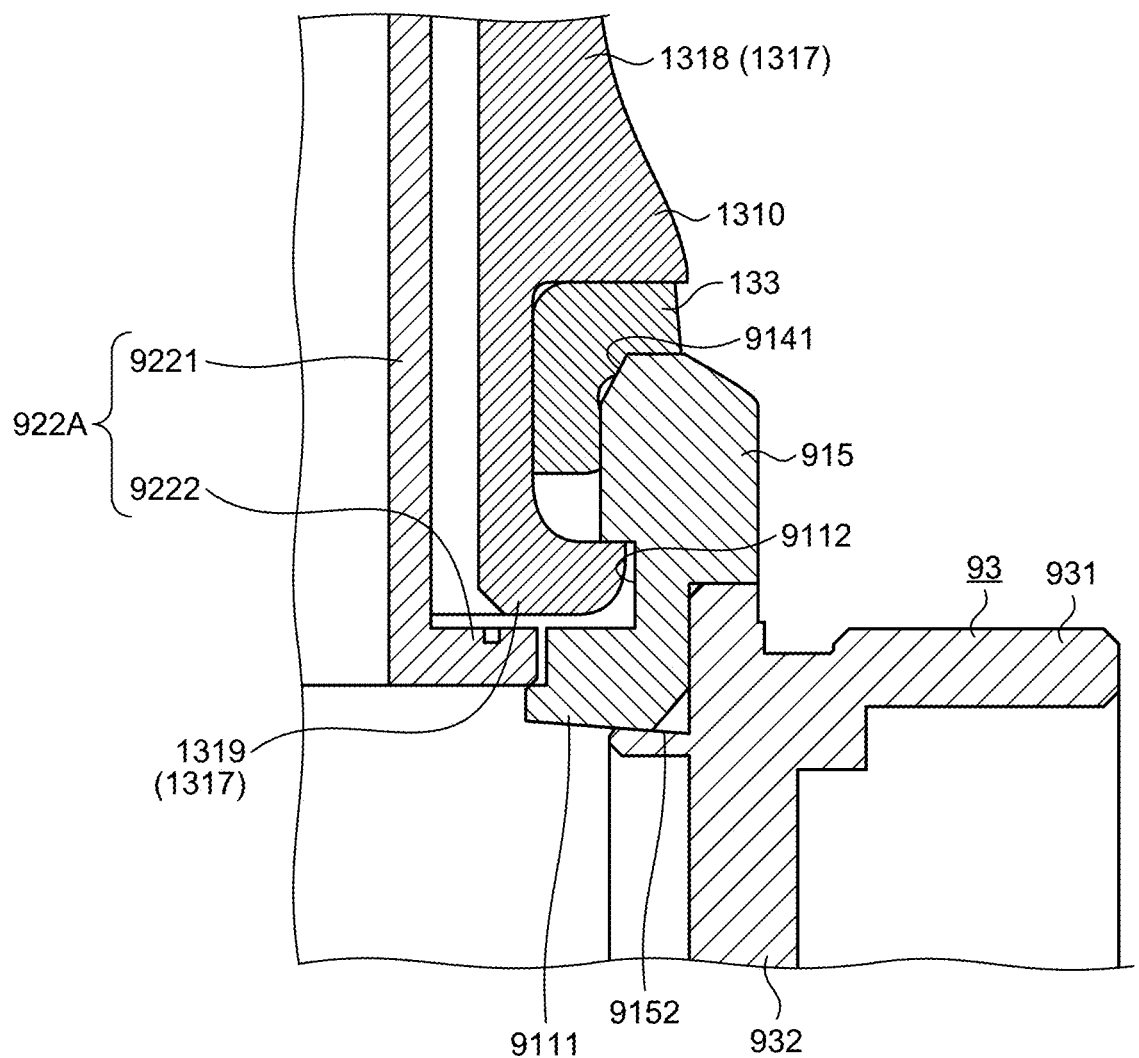
FIG. 8 is a view illustrating the imaging apparatus for endoscope according to the second embodiment.

FIGS. 6 to 8 are views illustrating an imaging apparatus 3A for endoscope according to the second embodiment. Specifically, FIG. 6 is a perspective view illustrating the appearance of the imaging apparatus 3A for endoscope. FIG. 7 is a cross-sectional view of the exterior casing 9A taken along a plane including the optical axis Ax0 of the endoscope 23. FIG. 8 is an enlarged view of a portion indicated by an arrow E in FIG. 7.

In the exterior casing 9A, as illustrated in FIGS. 6 to 8, the shapes of the exterior part main body 911 and the second exterior part 92 are changed from those of the exterior casing 9 described in the above-described first embodiment. Hereinafter, for convenience of description, the exterior part main body 911 according to the second embodiment will be referred to as an exterior part main body 911A. In addition, the second exterior part 92 according to the second embodiment will be referred to as a second exterior part 92A.

In the exterior part main body 911A, the shape of the end of the rectangular frame shape on the second exterior part 92A side (upper side in FIG. 7) configured by the four side walls 915 to 918 is different from that of the exterior part main body 911 described in the above-described first embodiment.

Specifically, as illustrated in FIG. 7 or 8, a rectangular frame-shaped first flange 9111 which projects from the inner surface and extends over the entire circumference of the edge of the second opening 9141 when viewed along the optical axis Ax0 of the endoscope 23 is provided on the inner surface of the rectangular frame-shaped end. The first flange 9111 corresponds to a flange according to the present disclosure. Further, as illustrated in FIG. 7 or 8, the projecting end portion of the rectangular frame-shaped first flange 9111 is formed in a stepped shape such that the inner dimension of the rectangular frame shape is larger on the side away from the second opening 9141 than on the side close to the second opening 9141.

In addition, on the inner surface of the end of the rectangular frame shape, at a position closer to the second opening 9141 than the first flange 9111, as illustrated in FIG. 7 or 8, a recess for engagement 9112 of a rectangular frame shape recessed toward the outside of the rectangular frame shape is provided.

In the second exterior part 92A, the shapes of the base part 921 and the protruding part 922 are changed from the shapes of the second exterior part 92A described in the above-described first embodiment. Hereinafter, for convenience of description, the base part 921 according to the second embodiment will be referred to as a base part 921A. In addition, the protruding part 922 according to the second embodiment will be referred to as a protruding part 922A.

When viewed along the optical axis Ax0 of the endoscope 23, the base part 921A is formed in a rectangular shape having an outer shape size smaller than an inner shape size of a rectangular frame constituted by the projecting end of the first flange 9111.

As illustrated in FIG. 7, the protruding part 922A includes a protruding part main body 9221 and a second flange 9222.

The protruding part main body 9221 has a rectangular frame shape protruding from an outer edge portion of one plate surface of the base part 921A in the normal direction of the plate surface. As illustrated in FIG. 7, the length dimension in the protrusion direction of the protruding part main body 9221 is longer than the length dimension on the second opening 9141 side than the first flange 9111 at the end of the rectangular frame shape on the second exterior part 92A side (upper side in FIG. 7) configured by the four side walls 915 to 918.

The second flange 9222 has a rectangular frame shape projecting from an outer surface of a projecting end portion of the rectangular frame-shaped protruding part main body 9221 toward the outside of the rectangular frame shape, and the projecting end portion may be fitted to the projecting end portion of the first flange 9111.

Then, the second exterior part 92A is fixed to the exterior part main body 911A by welding a projecting end portion of the second flange 9222 and a projecting end portion of the first flange 9111 in a state where the projecting end portion of the second flange 9222 is fitted to the projecting end portion of the first flange 9111. In this state, the protruding part main body 9221 faces the recess for engagement 9112. Note that the protruding part main body 9221 corresponds to a wall according to the present disclosure.

In the operating unit 13, as illustrated in FIGS. 6 to 8, the shapes of the button frame 1311 constituting the button unit 131 are changed from those of the operating unit 13A described in the above-described first embodiment. Hereinafter, for convenience of description, the button unit 131 and the button frame 1311 according to the second embodiment will be referred to as a button unit 131A and a button frame 1311A, respectively.

As illustrated in FIGS. 6 to 8, the button frame 1311A includes a button frame main body 1316 (FIGS. 6 and 7) and a concealment part 1317.

When viewed along the optical axis Ax0 of the endoscope 23, the button frame main body 1316 is formed of a rectangular plate body which is slightly larger than an outer shape size of the base part 921A having an outer shape size smaller than an inner shape size of a rectangular frame constituted by the projecting end of the first flange 9111. In addition, as illustrated in FIG. 7, the button frame main body 1316 is provided with an opening 1313, a recess 1314, and an insertion hole 1315 similar to those of the button frame 1311 described in the above-described first embodiment. Note that according to the second embodiment, only one recess 1314 and one insertion hole 1315 are provided.

As illustrated in FIG. 7 or 8, the concealment part 1317 includes a concealment part main body 1318 and an engagement claw 1319.

The concealment part main body 1318 has a rectangular frame shape protruding from an outer edge portion of one plate surface of the button frame main body 1316 in the normal direction of the plate surface. As illustrated in FIG. 7, the length dimension of the concealment part main body 1318 in the protrusion direction is set to be substantially the same as the length dimension of the protruding part main body 9221 in the protrusion direction.

On an outer surface of the concealment part main body 1318 having a rectangular frame shape, a rectangular frame-shaped pressing part 1310 bulging outward of the rectangular frame shape is provided. The surface of the pressing part 1310 on the protrusion direction side of the concealment part main body 1318 is formed of a flat surface substantially orthogonal to the protrusion direction.

The engagement claw 1319 has a rectangular frame shape projecting from an outer surface of a projecting end portion of the rectangular frame-shaped concealment part main body 1318 toward the outside of the rectangular frame shape, and the projecting end portion enters the recess for engagement 9112 so as to be engaged by the recess for engagement 9112.

In the second embodiment, the engagement claw 1319 is provided over the entire circumference of the concealment part main body 1318 having a rectangular frame shape, but the present disclosure is not limited thereto, and a plurality of engagement claws may be provided at predetermined intervals in the entire circumference of the concealment part main body 1318 having a rectangular frame shape.

Then, the button unit 131A is attached to the exterior casing 9A as described below.

The operator moves the button unit 131A such that the second exterior part 92A is inserted into the button frame 1311A from the upper side of the second exterior part 92A in FIG. 7. Then, the operator engages the engagement claw 1319 with the recess for engagement 9112 while interposing the packing 133 between the pressing part 1310 and the rectangular frame-shaped end on the second exterior part 92A side configured by the four side walls 915 to 918. Further, the operator fastens the screw Sc to the nut Nu through the insertion hole 1315. Thus, the button unit 131A is attached to the exterior casing 9A. In this state, the button unit 131A is stacked on the second exterior part 92A along the optical axis Ax0 of the endoscope 23, and conceals a connection portion (welded portion) between the projecting end portion of the second flange 9222 and the projecting end portion of the first flange 9111.

According to the second embodiment described above, the following effects are obtained in addition to the same effects as those of the first embodiment described above.

In the imaging apparatus 3A for endoscope according to the second embodiment, the second exterior part 92A is fixed to the exterior part main body 911A by welding between the projecting end portion of the second flange 9222 and the projecting end portion of the first flange 9111.

Therefore, it is difficult to visually recognize the welded portion from the outside, and the design of the imaging apparatus 3A for endoscope may be improved.

In particular, the button unit 131A is stacked on the second exterior part 92A along the optical axis Ax0 of the endoscope 23, and conceals a connection portion (welded portion) between the projecting end portion of the second flange 9222 and the projecting end portion of the first flange 9111.

Therefore, the welded portion may not be visually recognized from the outside, and the design of the imaging apparatus 3A for endoscope may be further improved.

Furthermore, in the imaging apparatus 3A for endoscope according to the second embodiment, the button unit 131A is engaged with the recess for engagement 9112.

Therefore, the number of the nuts Nu and the screws Sc for fixing the button unit 131A to the second exterior part 92A may be greatly reduced. In the second embodiment, the number of the nuts Nu and the number of the screws Sc are one, but the number of the nuts Nu and the number of the screws Sc are not limited thereto, and may be "0".

In addition, the recess for engagement 9112 is provided at a position close to a welded portion between the projecting end portion of the second flange 9222 and the projecting end portion of the first flange 9111. That is, the heat capacity at a position close to the welded portion is reduced in the recess for engagement 9112.

For this reason, the structure becomes the one where heat transfer does not occur easily to the recess for engagement 9112 side during welding of the welded portion, and the welded portion may be firmly welded.

In addition, in the imaging apparatus 3A for endoscope according to the second embodiment, the second exterior part 92A includes the protruding part main body 9221 facing the recess for engagement 9112 with a part of the button unit 131A interposed therebetween.

Accordingly, thermal deformation of button frame 1311A may be suppressed by protruding part main body 9221, so as to prevents the engagement claw 1319 from being easily apart from the recess for engagement 9112.

Other Embodiments

Although the embodiments for carrying out the present disclosure have been described so far, the present disclosure should not be limited only by the first and second embodiments described above.

Figure 9:
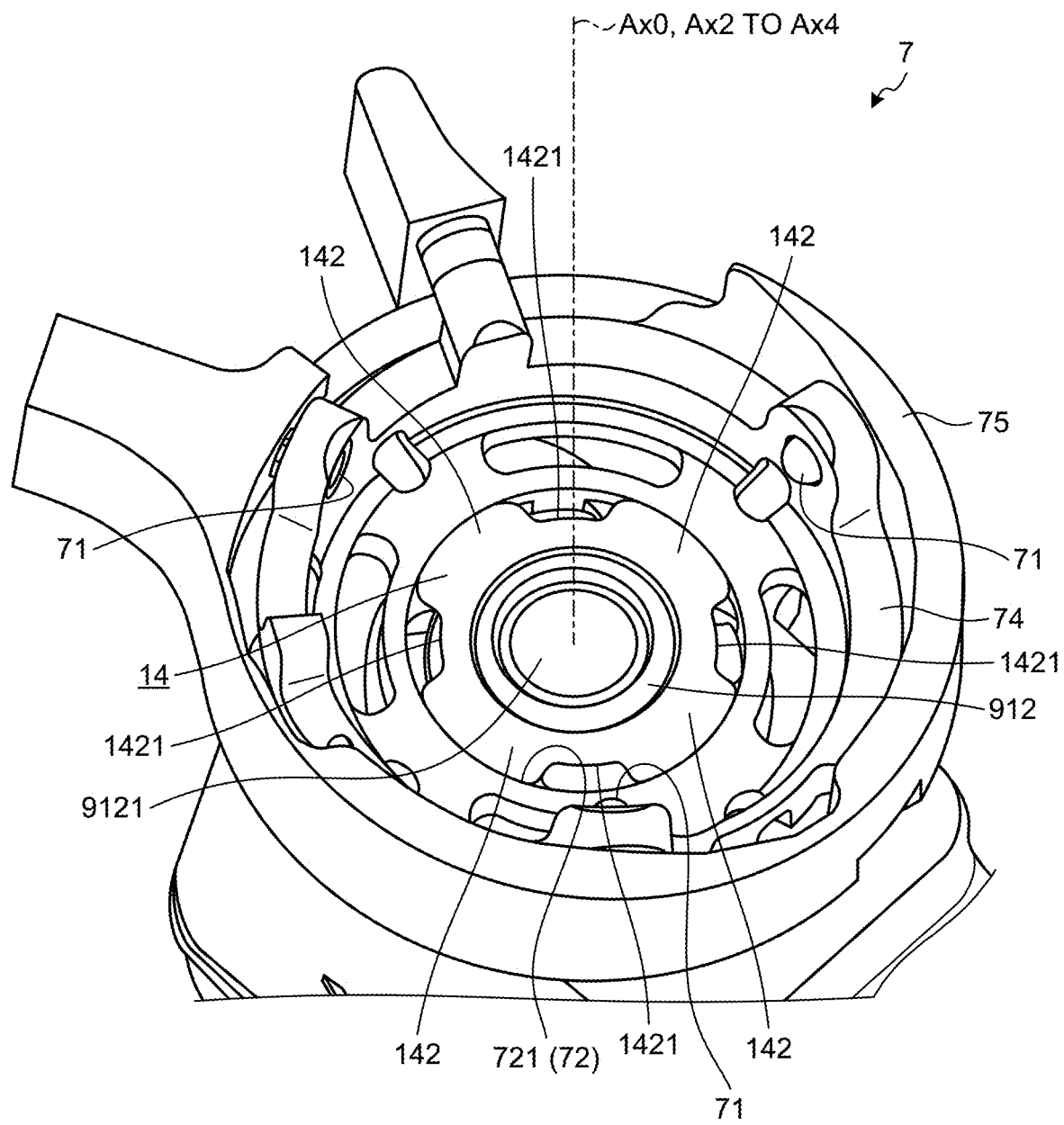
FIG. 9 is a view illustrating a first modification of the first and second embodiments.
Figure 10:
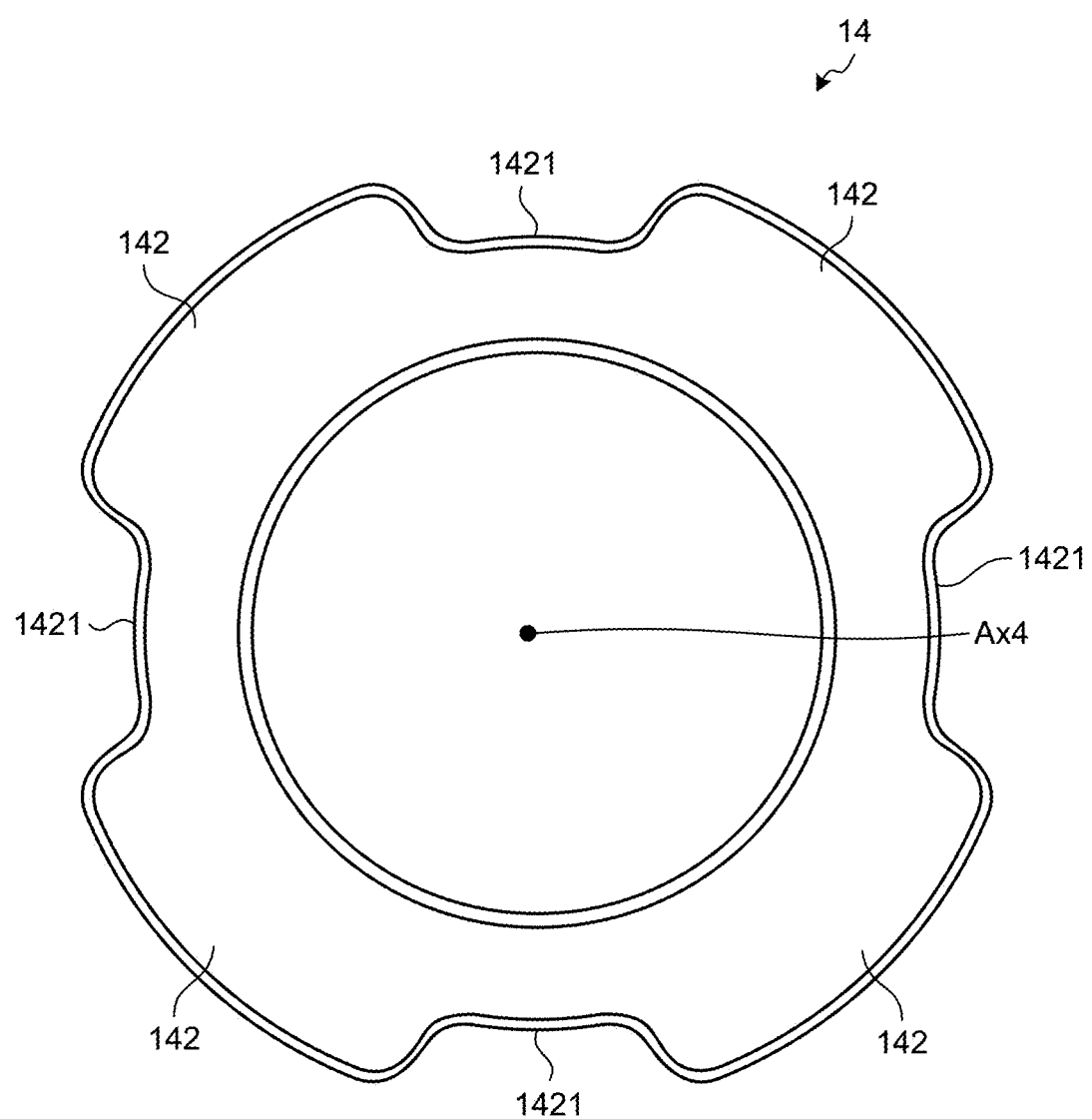
FIG. 10 is a view illustrating the first modification of the first and second embodiments.
Figure 11:
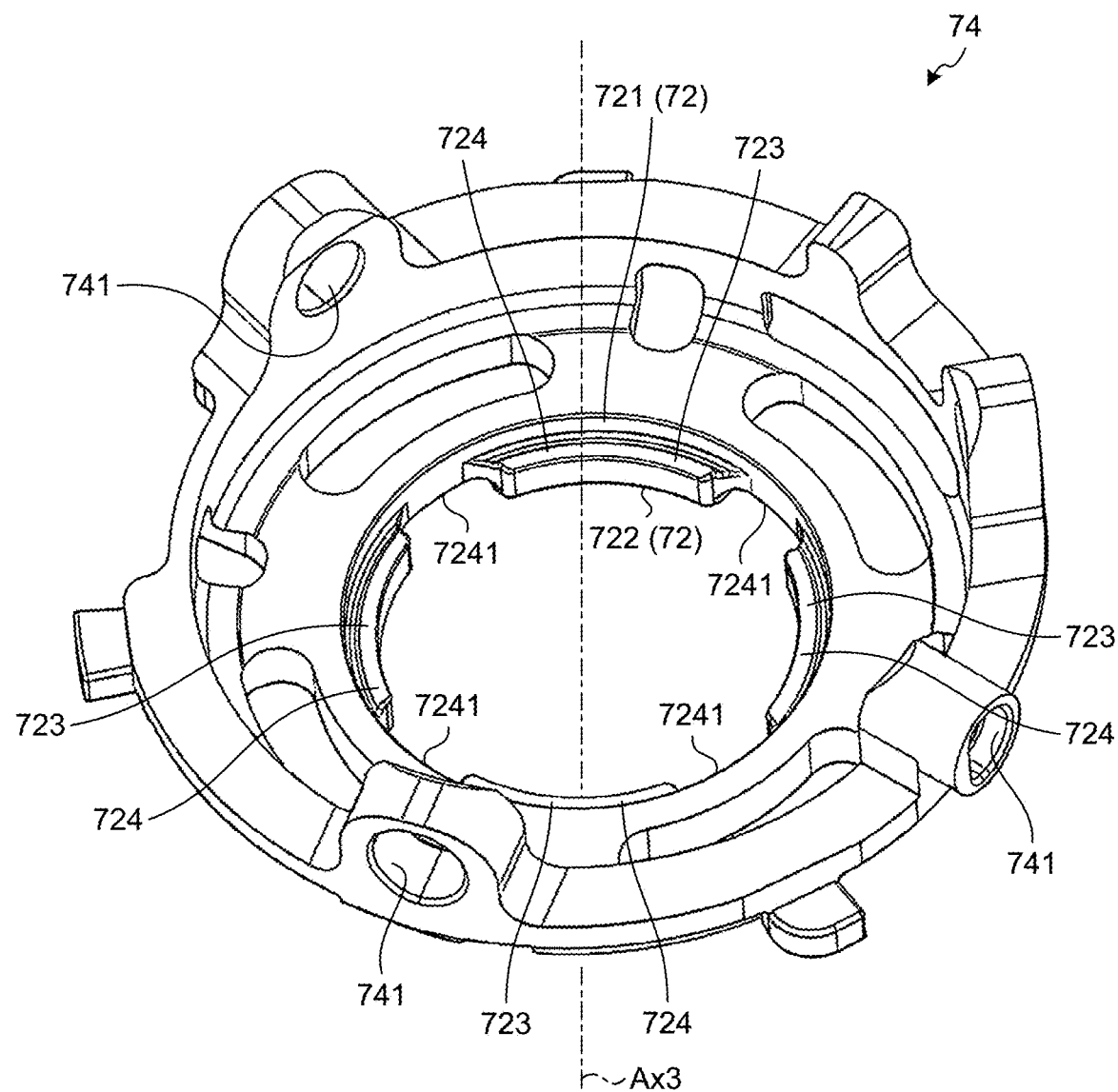
FIG. 11 is a view illustrating the first modification of the first and second embodiments.
Figure 12:
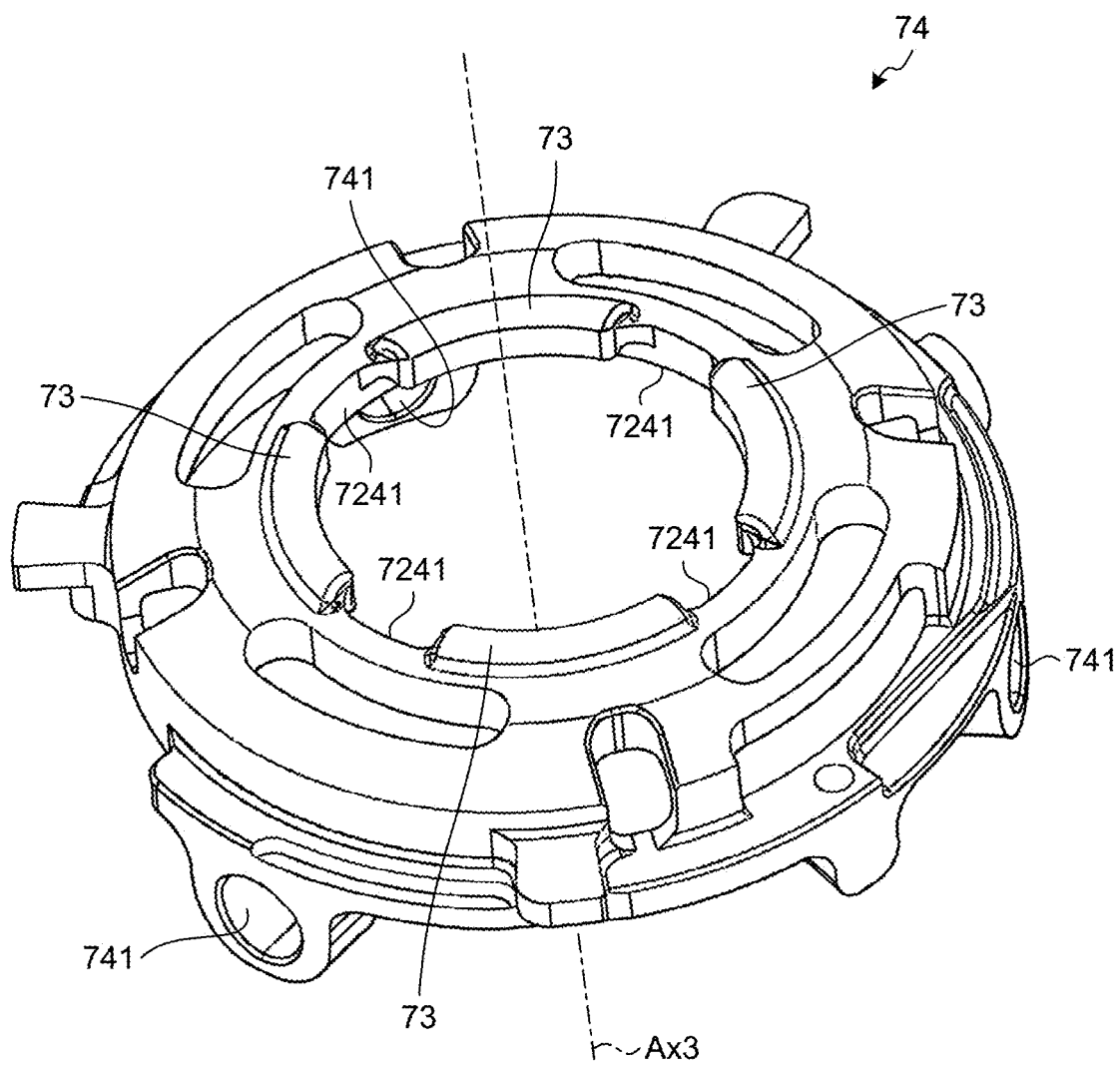
FIG. 12 is a view illustrating the first modification of the first and second embodiments.

FIGS. 9 to 13 are views illustrating a first modification of the first and second embodiments. Specifically, FIG. 9 is a perspective view of the coupler 7 according to the first modification as viewed from the side where the eyepiece 232 is located. FIG. 10 is a view of the mounting bush 14 according to the first modification as viewed from the side where the eyepiece 232 is located along the optical axis Ax0 of the endoscope 23. FIG. 11 is a perspective view of a mounting part 74 constituting the coupler 7 according to the first modification as viewed from the side where the eyepiece 232 is located. FIG. 12 is a perspective view of the mounting part 74 as viewed from the side where the imaging apparatus main body 6 is located. FIG. 13 is a cross-sectional view of a connection portion between the coupler 7 and the imaging apparatus main body 6 according to the first modification cut along a plane including the optical axis Ax0 of the endoscope 23.

In the first and second embodiments described above, the coupler 7 and the mounting bush 14 according to the first modification illustrated in FIGS. 9 to 13 may be adopted.

As illustrated in FIGS. 9 and 11 to 13, the coupler 7 according to the first modification includes the mounting part 74 and an operation ring 75.

The mounting part 74 is a portion that holds the endoscope 23, and has a bottomed cylindrical shape in which the eyepiece 232 may be fitted. The mounting part 74 includes a metal such as aluminum, an aluminum alloy, stainless steel, titanium, or a titanium alloy.

As illustrated in FIGS. 9 and 11 to 13, the through hole 72 is provided in a bottom portion of the mounting part 74. On the outer surface of the mounting part 74, the peripheral edge portion of the through hole 72 is the coupler-side slide surface 73.

The through hole 72 is a circular hole centered on the central axis Ax3 of the mounting part 74, and has a stepped shape having a first hole 721 on the side where the eyepiece 232 is located (the front side of FIG. 11) and a second hole 722 on the side where the imaging apparatus main body 6 is located (the back side of FIG. 11) as illustrated in FIG. 11. The inner diameter dimension of the first hole 721 is larger than the inner diameter dimension of the second hole 722. Hereinafter, for convenience of description, a stepped portion (connection portion between the first hole 721 and the second hole 722) in the through hole 72 is referred to as a stepped surface 723 (FIG. 11). An annular portion constituting the stepped surface 723 and the second hole 722 is referred to as a bush engagement part 724 (FIG. 11).

Here, as illustrated in FIG. 11, the bush engagement part 724 is provided with a plurality of (four in the first modification) first notches 7241 each notched in a direction away from the central axis Ax3 of the mounting part 74. That is, the bush engagement part 724 (stepped surface 723) is divided into a plurality of portions along the circumferential direction around the central axis Ax3 of the mounting part 74 by the plurality of first notches 7241.

The plurality of first notches 7241 is provided at positions that are rotationally symmetric about the central axis Ax3 of the mounting part 74 (positions that are rotationally symmetric by 90° in the first modification).

That is, similarly to the bush engagement part 724, the coupler-side slide surface 73 is also divided into a plurality of portions along the circumferential direction around the central axis Ax3 of the mounting part 74 by the plurality of first notches 7241 described above, as illustrated in FIG. 12. As illustrated in FIG. 13, these coupler-side slide surfaces 73 have a semicircular shape in which a cross section cut along a plane including the central axis Ax3 of the mounting part 74 bulges toward the casing-side slide surface 9101. Similarly, the stepped surface 723 has a semicircular shape in which a cross section cut along a plane including the central axis Ax3 of the mounting part 74 bulges toward the flange 142.

In addition, as illustrated in FIG. 11 or 12, the mounting part 74 is provided with a plurality of (three in the first modification) through holes 741 each penetrating from the outer peripheral surface to the inside of the mounting part 74, and a plurality of (three in the first modification) pressing parts 71 are arranged in the through holes 741. The plurality of through holes 741 are provided at positions that are rotationally symmetric about the central axis Ax3 of the mounting part 74 (positions that are rotationally symmetric by 120° in the first modification).

The operation ring 75 has an annular shape whose center matches the central axis Ax3 of the mounting part 74. The operation ring 75 includes a metal such as aluminum, an aluminum alloy, stainless steel, titanium, or a titanium alloy. The operation ring 75 faces the outer peripheral surface of the mounting part 74 and is attached to the mounting part 74 so as to be rotatable about the central axis Ax3 of the mounting part 74.

Here, as illustrated in FIG. 10, in the mounting bush 14 according to the first modification, the flange 142 is provided with a plurality of (four in the first modification) second notches 1421 each notched in a direction close to a central axis Ax4 of the mounting bush 14. That is, the flange 142 is divided into a plurality of portions along the circumferential direction around the central axis Ax4 of the mounting bush 14 by the plurality of second notches 1421.

The plurality of second notches 1421 is provided at positions that are rotationally symmetric about the central axis Ax4 of the mounting bush 14 (positions that are rotationally symmetric by 90° in the first modification).

The coupler 7 according to the first modification is attached to the imaging apparatus main body 6 as described below.

With regard to the coupler 7, the operator inserts the front exterior part 912 into the through hole 72 in a posture in which the opening of the mounting part 74 having the bottomed cylindrical shape is separated from the imaging apparatus main body 6. Then, the operator fixes the mounting bush 14 to the front exterior part 912 by fastening a screw groove provided in the small diameter surface 9123 and a screw groove provided in the inner peripheral surface of the bush main body 141. Thus, the coupler 7 is attached to the imaging apparatus main body 6. In this state, the central axis Ax3 of the mounting part 74 substantially coincides with the central axis Ax2 of the front exterior part 912. Further, a specific clearance is provided between the casing-side slide surface 9101 and the coupler-side slide surface 73. Then, the coupler 7 is rotatable about the optical axis Ax0 of the endoscope 23 with respect to the imaging apparatus main body 6.

In addition, the endoscope 23 is connected to the coupler 7 according to the first modification as described below.

After fitting the eyepiece 232 into the mounting part 74, the operator rotates the operation ring 75 in a first direction about the central axis Ax3 of the mounting part 74. As a result, each of the plurality of pressing parts 71 moves in the plurality of through holes 741, and protrudes into the mounting part 74. Then, each of the plurality of pressing parts 71 abuts on the outer peripheral surface of the eyepiece 232. That is, the fitted state is locked.

On the other hand, the endoscope 23 is detached from the coupler 7 as described below.

The operator rotates the operation ring 75 in a second direction opposite to the first direction about the central axis Ax3 of the mounting part 74. As a result, each of the plurality of pressing parts 71 may move toward the outside of the mounting part 74 in the plurality of through holes 741. That is, the lock state described above is released.

According to the first modification described above, the following effects are obtained in addition to the same effects as those of the first and second embodiments described above.

In the first modification, the coupler 7 is provided with the plurality of first notches 7241 described above. Further, the mounting bush 14 is provided with the plurality of second notches 1421 described above.

Therefore, when the imaging apparatus 3(3A) for endoscope is immersed in the cleaning solution and the imaging apparatus main body 6 and the coupler 7 are relatively rotated about the optical axis Ax0 of the endoscope 23, the cleaning solution flows in as described below.

That is, the cleaning solution flows into between the mounting bush 14 and the first hole 721, the second hole 722, and the stepped surface 723 through the first notch 7241 and the second notch 1421. Therefore, it is possible to efficiently clean between the mounting bush 14 and the first hole 721, the second hole 722, and the stepped surface 723.

Figure 14:
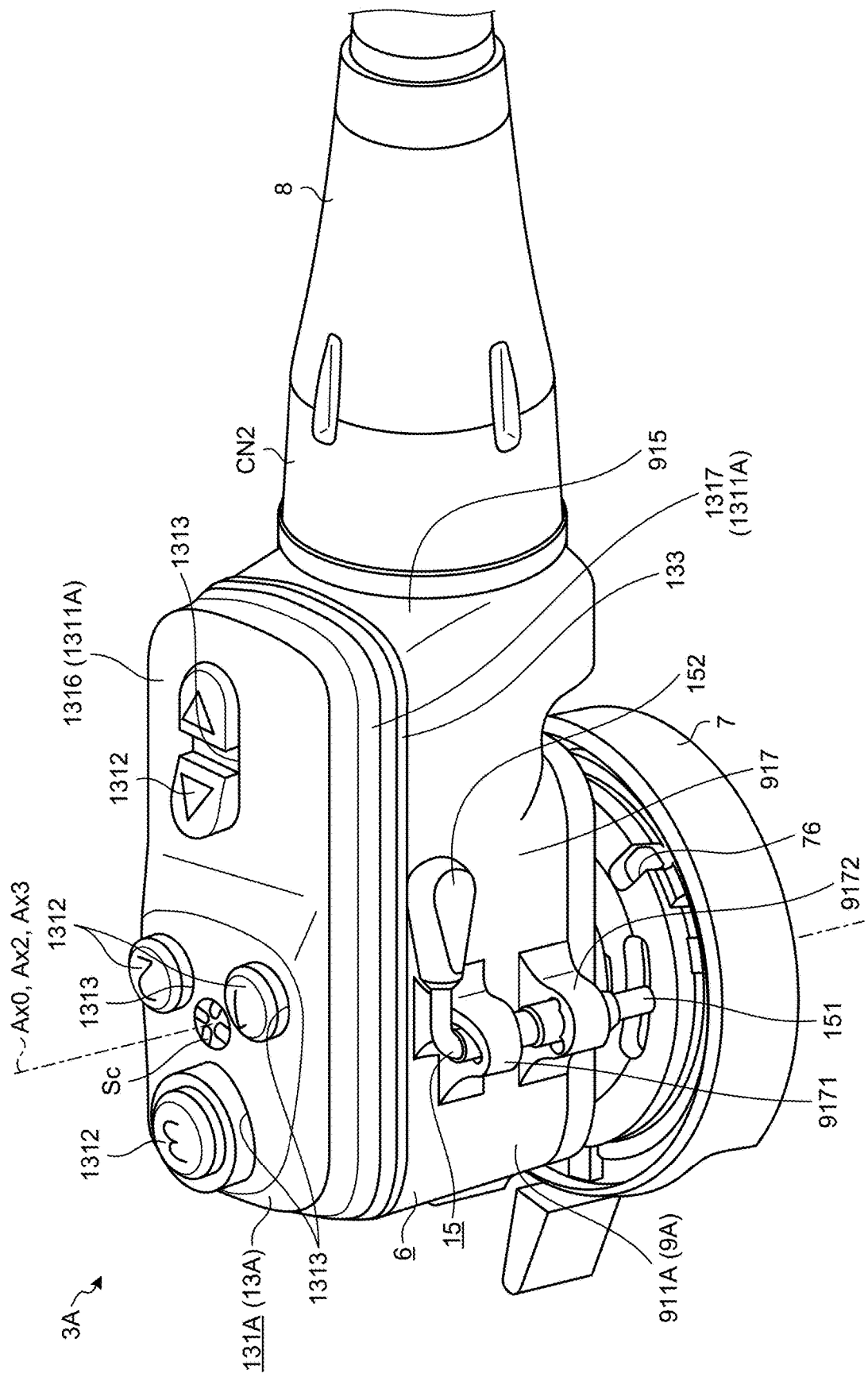
FIG. 14 is a view illustrating a second modification of the second embodiment.

FIG. 14 is a view illustrating a second modification of the second embodiment. Specifically, FIG. 14 is a view corresponding to FIG. 6.

In the imaging apparatus 3A for endoscope according to the second embodiment described above, a rotation restricting mechanism 15 according to the second modification illustrated in FIG. 14 may be adopted.

Here, as illustrated in FIG. 14, a plurality of rotation restricting holes 76 is provided in the bottom portion of the coupler 7. The plurality of rotation restricting holes 76 is provided at positions that are rotationally symmetric about the central axis Ax3 of the coupler 7.

In the exterior part main body 911A, a pair of support parts 9171 and 9172 for supporting the rotation restricting mechanism 15 is provided on the outer surface of a side wall 917. The pair of support parts 9171 and 9172 is provided side by side in the direction along the optical axis Ax0 of the endoscope 23 on the outer surface of the side wall 917.

The rotation restricting mechanism 15 is switched to a rotation restricting state in which the relative rotation between the imaging apparatus main body 6 and the coupler 7 about the optical axis Ax0 of the endoscope 23 is restricted or a rotation permitting state in which the rotation is permitted according to the operation by the user such as a doctor. As illustrated in FIG. 14, the rotation restricting mechanism 15 includes a restricting pin 151, an operation lever 152, and a biasing member (not illustrated).

The restricting pin 151 is a columnar pin that may be inserted into the rotation restricting holes 76, and is supported to be movable in a direction along the optical axis Ax0 of the endoscope 23 with respect to the pair of support parts 9171 and 9172.

The operation lever 152 is a portion that receives an operation by a user such as a doctor, is provided at an end of the restricting pin 151 on a side away from the coupler 7, and extends while being bent in a direction substantially orthogonal to the extending direction of the restricting pin 151.

The above-described biasing member is formed of a coil spring or the like. Then, the biasing member is provided in a state of being exposed to the outside from between the pair of support parts 9171 and 9172, and constantly biases the restricting pin 151 toward the coupler 7.

Note that FIG. 14 illustrates a state in which the rotation restricting mechanism 15 is set to the rotation permitting state.

When the user such as a doctor rotates the operation lever 152 about the central axis of the restricting pin 151 from the state illustrated in FIG. 14, the restricting pin 151 moves toward the coupler 7 together with the operation lever 152 by the biasing force of the biasing member described above. When the restricting pin 151 is inserted into the rotation restricting hole 76, the rotation restricting mechanism 15 is set to the rotation restricting state. Further, if the operation lever 152 is rotated from the initial state to the position illustrated in FIG. 14, the restricting pin 151 moves in a direction away from the coupler 7 together with the operation lever 152 against the biasing force of the biasing member described above. Then, when the restricting pin 151 is removed from the rotation restricting hole 76, the rotation restricting mechanism is set to the rotation permitting state.

According to the second modification described above, the following effects are obtained in addition to the same effects as those of the second embodiment described above.

In the rotation restricting mechanism 15 according to the second modification, the above-described biasing member is exposed to the outside from between the pair of support parts 9171 and 9172.

Therefore, if the imaging apparatus 3A for endoscope is immersed in the cleaning solution, the biasing member may be effectively cleaned with the cleaning solution.

Note that the rotation restricting mechanism 15 according to the second modification may be adopted in the imaging apparatus 3 for endoscope according to the first embodiment described above.

In the first and second embodiments described above, the case where the imaging apparatuses 3 and 3A for endoscope according to the present disclosure are used for the resectoscope 2 has been exemplified, but the present disclosure is not limited thereto, and the imaging apparatuses 3 and 3A for endoscope may be used for other various endoscopes (rigid endoscope and flexible endoscope).

In the first and second embodiments described above, the operation board 132 constituting the operating units 13 and 13 A is provided outside the exterior casings 9 and 9A, but the present disclosure is not limited thereto. For example, if the operation board 132 may detect the button operation by the user using the magnetic force, the operation board 132 may be provided in the exterior casings 9 and 9A. At this time, the hermetic connector 134 is unnecessary.

Note that the following configurations also belong to the technical scope of the present disclosure.

(1) An imaging apparatus for endoscope including: a coupler configured to hold an endoscope for capturing an image of a subject, and emit the image of the subject; an exterior casing connected to the coupler and extending along a first axis crossing an optical axis of the endoscope, the exterior casing having outer dimensions in a direction along the first axis greater than outer dimensions in a direction along the optical axis of the endoscope; an optical system configured to guide light of the image of the subject; and an imaging unit configured to capture the image of the subject through the optical system, wherein the exterior casing includes a first exterior part including a first side wall and a second side wall crossing the optical axis of the endoscope, a first opening in the first side wall, a second opening in the second side wall which is further away from the coupler than the first side wall, and a third opening in a third side wall crossing the first axis, a second exterior part connected to the first exterior part to seal the second opening side of the first exterior part, and a connector part connected to the first exterior part to seal the third opening side of the first exterior part and is configured to connect to a cable for transmitting an image signal output from the imaging unit, and the optical system and the imaging unit are housed, in the exterior casing, side by side on the optical axis of the endoscope such that the light of the image of the subject guided by the optical system is captured by the imaging unit.

(2) The imaging apparatus for endoscope according to (1), wherein the second opening has an opening area larger than an opening area of the third opening, and the optical system and the imaging unit are housed in the exterior casing from the second opening.

(3) The imaging apparatus for endoscope according to (1) or (2), wherein the first side wall and the second side wall include surfaces that face each other, and the first opening and the second opening are provided in the surfaces that face each other.

(4) The imaging apparatus for endoscope according to any one of (1) to (3), further including a circuit substrate configured to process an image signal output from the imaging unit, wherein the circuit substrate is housed in the exterior casing at a position away from the optical axis of the endoscope.

(5) The imaging apparatus for endoscope according to any one of (1) to (4), further including: a button unit including a button configured to receive an operation by a user; and a ring-shaped sealing member, wherein the button unit is fixed to an outer surface of the second exterior part through the sealing member in a state in which the button unit is stacked on the second exterior part along the optical axis of the endoscope.

(6) The imaging apparatus for endoscope according to any one of (1) to (5), wherein the first exterior part includes a ring-shaped flange protruding from an inner surface of each of the side walls connected to the second side wall and extending over an entire circumference of an edge of the second opening when viewed along the optical axis of the endoscope, and the second exterior part includes an outer edge portion connected to the flange to seal the second opening side of the first exterior part.

(7) The imaging apparatus for endoscope according to (6), further including a button unit including a button for receiving the operation by the user, wherein the button unit is fixed to an outer surface of the second exterior part in a state in which the button unit is stacked on the second exterior part along the optical axis of the endoscope, and configured to conceal a portion at which the second exterior part and the flange are connected to each other.

(8) The imaging apparatus for endoscope according to (7), wherein the inner surface of each of the side walls connected to the second side wall includes a recess for engagement that is located closer to the second opening side than the flange and is to engage with the button unit.

(9) The imaging apparatus for endoscope according to (8), wherein the second exterior part includes a wall that faces the recess for engagement with a part of the button unit interposed therebetween.

(10) An imaging system including: an endoscope configured to capture an image of a subject, and emit the image of the subject; and an imaging apparatus for endoscope connected to the endoscope and configured to capture the image of the subject emitted from the endoscope, wherein the imaging apparatus for endoscope includes a coupler configured to hold the endoscope, an exterior casing connected to the coupler and extending along a first axis crossing an optical axis of the endoscope, the exterior casing having outer dimensions in a direction along the first axis greater than outer dimensions in a direction along the optical axis of the endoscope, an optical system configured to guide light of the image of the subject, and an imaging unit configured to capture the image of the subject through the optical system, and the exterior casing includes a first exterior part including a first side wall and a second side wall crossing the optical axis of the endoscope, a first opening in the first side wall, a second opening in the second side wall which is further away from the coupler than the first side wall, and a third opening in a third side wall crossing the first axis, a second exterior part connected to the first exterior part to seal the second opening side of the first exterior part, and a connector part connected to the first exterior part to seal the third opening side of the first exterior part and is configured to connect to a cable for transmitting an image signal output from the imaging unit, and the optical system and the imaging unit are housed, in the exterior casing, side by side on the optical axis of the endoscope so that the light of the image of the subject guided by the optical system is captured by the imaging unit.

(11) The imaging system according to (10), wherein the second opening has an opening area larger than an opening area of the third opening, and the optical system and the imaging unit are housed in the exterior casing from the second opening.

(12) The imaging system according to (10) or (11), wherein the first side wall and the second side wall include surfaces that face each other, and the first opening and the second opening are provided in the surfaces that face each other.

(13) The imaging system according to any one of (10) to (12), wherein the endoscope is an endoscope used for resectoscope, and the coupler and the exterior casing are connected to be relatively rotatable around the optical axis of the endoscope.

(14) The imaging system according to (13), wherein a center position of the connector part is located at a position closer to the endoscope than a center position in a direction along the optical axis of the endoscope in the exterior casing.

According to the imaging apparatus for endoscope according to the present disclosure, assemblability may be improved without losing optical performance.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An imaging apparatus for an endoscope comprising:
   a coupler configured to
      hold an endoscope for capturing an image of a subject, and
      emit the image of the subject;
   an exterior casing connected to the coupler and extending along a first axis crossing an optical axis of the endoscope, the exterior casing having outer dimensions in a direction along the first axis greater than outer dimensions in a direction along the optical axis of the endoscope;
   an optical system configured to guide light of the image of the subject; and
   an image sensor configured to capture the image of the subject through the optical system, wherein
   the exterior casing includes
      a first exterior part including
         a first side wall and a second side wall crossing the optical axis of the endoscope,
         a first opening in the first side wall,
         a second opening in the second side wall which is further away from the coupler than the first side wall, and a third opening in a third side wall crossing the first axis,
a second exterior part connected to the first exterior part to seal the second opening of the first exterior part, and
a connector part connected to the first exterior part to seal the third opening of the first exterior part and is configured to connect to a cable for transmitting an image signal output from image sensor, and
the optical system and the image sensor are housed, in the exterior casing, side by side on the optical axis of the endoscope such that the light of the image of the subject guided by the optical system is captured by the image sensor.

2. The imaging apparatus for an endoscope according to claim 1, wherein
the second opening has an opening area larger than an opening area of the third opening, and
the optical system and the image sensor are inserted into the exterior casing through the second opening.

3. The imaging apparatus for an endoscope according to claim 1, wherein
the first side wall and the second side wall include surfaces that face each other, and
the first opening and the second opening are provided in the surfaces that face each other.

4. The imaging apparatus for an endoscope according to claim 1, further comprising
a circuit substrate configured to process an image signal output from the image sensor, wherein
the circuit substrate is housed in the exterior casing at a position away from the optical axis of the endoscope.

5. The imaging apparatus for an endoscope according to claim 1, further comprising:
a button frame and a button configured to receive an operation by a user, the button being exposed by the button frame; and
a sealing member, wherein
the button frame is fixed to an outer surface of the second exterior part through the sealing member in a state in which the button frame is stacked on the second exterior part along the optical axis of the endoscope.

6. The imaging apparatus for an endoscope according to claim 1, wherein
the first exterior part includes a flange protruding from an inner surface of each of four side walls, including the third side wall, connected between the second side wall and the first side wall, the flange extending over an entire circumference of an edge of the second opening when viewed along the optical axis of the endoscope, and
the second exterior part includes an outer edge portion connected to the flange to seal the second opening of the first exterior part.

7. The imaging apparatus for an endoscope according to claim 6, further comprising a button frame and a button for receiving an operation by a user, the button being exposed by the button frame, wherein
the button frame is fixed to an outer surface of the second exterior part in a state in which the button frame is stacked on the second exterior part along the optical axis of the endoscope, and configured to conceal a portion at which the second exterior part and the flange are connected to each other.

8. The imaging apparatus for an endoscope according to claim 7, wherein
the inner surface of each of the four side walls connected between the second side wall and the first side wall, includes a recess for engagement that is located closer to the second opening than the flange and is to engage with the button frame.

9. The imaging apparatus for an endoscope according to claim 8, wherein
the second exterior part includes a wall that faces the recess for engagement with a part of the button frame interposed therebetween.

10. The imaging apparatus for an endoscope according to claim 1, wherein the third side wall includes a bulge at an angle to the first axis and extending toward the outside of the exterior casing, the third opening being in the bulge.

11. The imaging apparatus for an endoscope according to claim 1, further comprising a pair of support parts on opposite sides of an outer surface of the exterior casing along the optical axis of the endoscope to support a rotation restricting mechanism.

12. The imaging apparatus for an endoscope according to claim 1, further comprising an operation ring, the operating ring, in accordance with a rotational direction thereon, locks or releases the coupler to the exterior casing.

13. An imaging system comprising:
an endoscope configured to
capture an image of a subject, and
emit the image of the subject; and
an imaging apparatus connected to the endoscope and configured to capture the image of the subject emitted from the endoscope, wherein
the imaging apparatus includes
a coupler configured to hold the endoscope,
an exterior casing connected to the coupler and extending along a first axis crossing an optical axis of the endoscope, the exterior casing having outer dimensions in a direction along the first axis greater than outer dimensions in a direction along the optical axis of the endoscope,
an optical system configured to guide light of the image of the subject, and
an image sensor configured to capture the image of the subject through the optical system, and
the exterior casing includes
a first exterior part including
a first side wall and a second side wall crossing the optical axis of the endoscope,
a first opening in the first side wall,
a second opening in the second side wall which is further away from the coupler than the first side wall, and
a third opening in a third side wall crossing the first axis,
a second exterior part connected to the first exterior part to seal the second opening side of the first exterior part, and
a connector part connected to the first exterior part to seal the third opening of the first exterior part and is configured to connect to a cable for transmitting an image signal output from the image sensor, and
the optical system and the image sensor are housed, in the exterior casing, side by side on the optical axis of the endoscope so that the light of the image of the subject guided by the optical system is captured by the image sensor.

14. The imaging system according to claim 13, wherein
the second opening has an opening area larger than an opening area of the third opening, and
the optical system and the image sensor are housed in the exterior casing from the second opening.

15. The imaging system according to claim 13, wherein
the first side wall and the second side wall include surfaces that face each other, and
the first opening and the second opening are provided in the surfaces that face each other.

16. The imaging system according to claim 13, wherein
the endoscope is a resectoscope, and
the coupler and the exterior casing are connected to be relatively rotatable around the optical axis of the endoscope.

17. The imaging system according to claim 16, wherein
a center position of the connector part is located at a position closer to the endoscope than a center position in a direction along the optical axis of the endoscope in the exterior casing.

18. An imaging apparatus for endoscope comprising:
an exterior casing having a coupler side to be connected to a coupler configured to hold an endoscope for imaging a subject, wherein the exterior casing extends along a first axis crossing an optical axis of the endoscope, the exterior casing having outer dimensions in a direction along the first axis greater than outer dimensions in a direction along the optical axis of the endoscope;
the exterior casing includes
a first exterior part including
a first side wall and a second side wall crossing the optical axis of the endoscope,
a first opening in the first side wall, wherein the first side wall is the coupler side of the exterior casing;
a second opening in the second side wall, and
a third opening in a third side wall crossing the first axis,
a second exterior part connected to the first exterior part to seal the second opening side of the first exterior part, and
a connector part connected to the first exterior part to seal the third opening of the first exterior part and is configured to connect to a cable for transmitting an image signal output from an optical system and an image sensor housed in the exterior casing, side by side on the optical axis of the endoscope such that light of the image of the subject guided by the optical system is captured by the image sensor.

19. The imaging apparatus for an endoscope according to claim 18, wherein
the second opening has an opening area larger than an opening area of the third opening, and
the optical system and the image sensor are to be inserted into the exterior casing through the second opening.

20. The imaging apparatus for an endoscope according to claim 18, wherein
the first exterior part includes a flange protruding from an inner surface of each of four side walls, including the third side wall, connected between the second side wall and the first side wall, the flange extending over an entire circumference of an edge of the second opening when viewed along the optical axis of the endoscope, and
the second exterior part includes an outer edge portion connected to the flange to seal the second opening of the first exterior part.

* * * * *